US006575956B1

(12) United States Patent
Brisken et al.

(10) Patent No.: US 6,575,956 B1
(45) Date of Patent: Jun. 10, 2003

(54) METHODS AND APPARATUS FOR UNIFORM TRANSCUTANEOUS THERAPEUTIC ULTRASOUND

(75) Inventors: Axel F. Brisken, Fremont, CA (US); Robert Zuk, Atherton, CA (US); John R. McKenzie, San Carlos, CA (US); Mark W. Cowan, Fremont, CA (US)

(73) Assignee: Pharmasonics, Inc., Sunnyvale, CA (US)

( * ) Notice: Subject to any disclaimer, the term of this patent is extended or adjusted under 35 U.S.C. 154(b) by 0 days.

(21) Appl. No.: 09/435,095

(22) Filed: Nov. 5, 1999

Related U.S. Application Data

(63) Continuation-in-part of application No. 09/364,616, filed on Jul. 29, 1999, which is a continuation-in-part of application No. 09/255,290, filed on Feb. 22, 1999, which is a continuation-in-part of application No. 09/126,011, filed on Jul. 29, 1998.
(60) Provisional application No. 60/070,236, filed on Dec. 31, 1997.

(51) Int. Cl.⁷ ............................................. A61M 31/00
(52) U.S. Cl. ......................................... 604/500; 604/22
(58) Field of Search ..................... 604/20–22, 500–501, 604/93.01; 600/437–473; 601/2–3; 435/1.29, 93.1, 93.2, 520

(56) References Cited

U.S. PATENT DOCUMENTS

| 5,018,508 | A | | 5/1991 | Fry et al. | |
|---|---|---|---|---|---|
| 5,040,537 | A | | 8/1991 | Katakura | |
| 5,115,805 | A | * | 5/1992 | Bommannan et al. | ......... 601/2 |
| 5,197,946 | A | | 3/1993 | Tachibana | |
| 5,243,986 | A | | 9/1993 | Wurster | |
| 5,295,484 | A | | 3/1994 | Marcus et al. | |
| 5,490,840 | A | | 2/1996 | Uzgiris et al. | |
| 5,509,896 | A | | 4/1996 | Carter | |
| 5,580,575 | A | * | 12/1996 | Unger et al. | ................. 424/450 |
| 5,586,982 | A | * | 12/1996 | Abela | ........................... 606/14 |
| 5,656,016 | A | | 8/1997 | Ogden | |
| 5,658,247 | A | | 8/1997 | Henley | |
| 5,681,278 | A | | 10/1997 | Igo et al. | |
| 5,752,515 | A | | 5/1998 | Jolesz et al. | |
| 6,234,990 | B1 | * | 5/2001 | Rowe et al. | ................... 604/22 |

FOREIGN PATENT DOCUMENTS

| EP | 0 744 189 | 11/1996 |
|---|---|---|
| WO | WO 96/27341 | 9/1996 |
| WO | WO 96/29935 | 10/1996 |
| WO | WO 98/18391 | 5/1998 |
| WO | WO 98/48711 | 11/1998 |
| WO | WO 99/21584 | 5/1999 |
| WO | WO 00/18468 | 4/2000 |

OTHER PUBLICATIONS

Machluf et al., "A novel vector for gene transfection using ultrasound energy" (1998) Pediatrics 102(3):844 Abstract No. 43.
Kim et al., "Ultrasound–Mediated Transfection of Mammalian Cells", Human Gene Therapy, 7:1339–1346, Jul. 10, 1996.
He et al., "Application of Ultrasound Energy for Intracardiac Ablation of Arrhythmias", European Heart Journal, 16:961–966, 1995.
Mitragotri et al., "Ultrasound–Mediated Transdermal Protein Delivery", Science, 269:850–853, Aug. 11, 1995.

(List continued on next page.)

Primary Examiner—Brian L. Casler
Assistant Examiner—LoAn H. Thanh
(74) Attorney, Agent, or Firm—Townsend and Townsend and Crew LLP

(57) ABSTRACT

A wide beam ultrasound delivery system providing a uniform exposure field is used to enhance the uptake of injected substances and/or to enhance the transfection of DNA in the tissues of human subject, or reduce the amount of vascular intimal hyperplasia in human subjects following vascular injury.

31 Claims, 34 Drawing Sheets

OTHER PUBLICATIONS

Bommannan et al., "Sonophoresis. I. The Use of High–Frequency Ultrasound to Enhance Transdermal Drug Delivery", Pharmaceutical Research, 9(4):559–564, 1992.

Bommannan et al., Somophoresis. II. Examination of the Mechanism(s) of Ultrasound–Enhanced Transdermal Drug Delivery, Pharmaceutical Research, 9(8):1043–1047, 1992.

Enhancing Cell Transformation: The SonoPorator 100, Product Literature.

Tsurumi et al. "Direct intramuscular gene transfer of naked DNA encoding vascular endothelial growth factor augments collateral development and tissue perfusion" Circulation (1996) 94(12):3281–3290.

* cited by examiner

METHODS AND APPARATUS FOR UNIFORM TRANSCUTANEOUS THERAPEUTIC ULTRASOUND

CROSS-REFERENCES TO RELATED APPLICATIONS

The present it application is a continuation-in-part of Application Ser. No. 09/364,616, filed on Jul. 29, 1999, which is a continuation-in-part of Application Ser. No. 09/255,290, filed on Feb. 22, 1999, which is a continuation-in-part of Application Ser. No. 09/126,011, filed on Jul. 29, 1998.

The present application is also related to U.S. Pat. No. 6,210,393, issued Apr. 3, 2001, which claimed the benefit of Provisional Application 60/070,236, filed Dec. 31, 1997.

The present application is also related to U.S. Pat. No. 6,387,116, issued May 14, 2002, the full disclosures of which are incorporated herein by reference in their entirety for all purposes.

TECHNICAL FIELD

The present invention relates to ultrasound systems for delivering therapeutic ultrasound energy to a target region of a patient's body.

BACKGROUND OF THE INVENTION

A current standard technique for the delivery of drugs or other substances into the human body is needle injection, in particular, intramuscular injection (IM). A bolus containing the substance is typically injected into muscle where it diffuses through the interstitial fluid or pools between muscle layers and thence diffuses through the same or more distant interstitial fluid. This diffusion might spread over a length of five or more centimeters parallel to the muscle fibers and over a width of perhaps one or two centimeters normal to the fibers. Over a period of time, typically on the order of 10 to 100 minutes, the vascular system of the body takes over and flushes the substance out of the interstitial fluid and into the capillaries. From there, the cardiovascular system widely distributes the substance into the rest of the patient's body.

Newly developed drugs often have application only to specific organs or sections of organs. As such, systemic distribution of the drug throughout the remainder of the body can: (1) dilute very expensive drugs, weakening their effects, (2) generate an effect systemically instead of locally, and (3) widely distribute a drug which may be toxic to other organs in the body. Furthermore, some of the newly developed drugs include DNA in various forms, such DNA being degraded very rapidly by natural mechanisms in the body if delivered systemically, thus preventing a full dose from reaching the designated organ.

In vitro experiments by H. J. Kim, et. al. (Human Gene Therapy, 7, 1339–1346, Jul. 10, 1996) and in vivo experiments by S. Bao, et. al. (Cancer Research 58, 219–221, Jan. 15, 1998) have demonstrated enhanced transfection of DNA into human cell lines by supplementary application of lower frequency ultrasound. While the exact biological response to DNA in conjunction with ultrasound remains unclear, it is accepted that mechanical mechanisms are responsible for the temporary permeabilization of cell membranes and possibly cell nuclear membranes.

Accordingly, it would be desirable to provide ultrasonic devices, kits, and methods for delivering such site-specific drugs in a manner which enhances absorption and/or transfection specifically into the cells within the injection diffusion zone, specifically around the site of their delivery into a target region of a patient's body. Substances thus absorbed directly into the cells or further into the nucleus of the cells have maximum potency at or around the injection site and reduced diffusion throughout the remainder of the body. Furthermore, it would be desirable for the enhancement mechanism to be mechanical in origin, as compared to thermal in origin. Mechanical methods may function to temporally permeabilize cellular membranes as compared to thermal mechanisms which may give rise to tissue inflammation.

By way of example, it has been demonstrated that injection of plasmid DNA which expresses vascular endothelial growth factor (VEGF) promotes growth of collateral vessels in ischemic tissue. Exposure of the same muscle tissue to ultrasound in conjunction with these injections improves the cellular uptake and/or transfection and manifestation of the DNA. The current problem is that these DNA injections are typically directed to specific target muscles. The injection bolus typically follows the muscle fibers, spreading as described above. Furthermore, it has been demonstrated that natural bodily defense mechanisms degrade the potency of DNA, typically by as much as fifty percent in the matter of a few minutes.

Ultrasonic systems which might be ineffectively used for enhanced transfection of DNA or for the cellular uptake of other drugs by various biological cells do exist. Unfortunately, either these systems produce very narrow ultrasound beams due to operation in the focal zone or far field (Fraunhofer zone) or they produce broad irregular fields due to operation in the near field (Fresnel zone). In the first case, the narrow beams cannot deliver a satisfactory dose of ultrasound to the volume of tissue in a time frame short compared to the natural biological destruction of the DNA. In the second case, the irregular fields are characterized by large differences in acoustic intensity both in the lateral direction (parallel to the transducer surface) and in the axial direction (normal to the transducer surface), such differences leading to unpredictable amounts of ultrasound dose.

Systems which operate in the focal zone and far field (Fraunhofer zone) include medical diagnostic ultrasound imaging and Doppler systems. These feature very tight acoustic scanning beams for the purpose of achieving the highest possible lateral resolution. Furthermore, ultrasound tissue exposure in scanning beams is held to the frame rate of the system display, typically 30 Hz. Maximum signal strengths are limited by industry and FDA guidance protocols. These systems furthermore operate at higher frequencies, in the range where longer bursts of ultrasound or continuous ultrasound exposure would create a heating effect due to absorption of the ultrasound energy in the tissues. These systems would be incapable of delivering the mechanical ultrasound effects to achieve acceptable therapeutic effects.

Additional systems which operate with highly focused beams include low frequency lithotripters and high frequency thermal ablation systems. Lithotripters feature short bursts of high intensity ultrasound with a very low burst repetition rate. They cannot provide broad tissue coverage with a high duty cycle. Ablation systems, typically identified as high intensity focused ultrasound (HIFU) systems, function to create thermal lesions in living tissue. While their acoustic beams might be swept through tissue for wide area coverage, their high frequency operation fails to produce mechanical effects in tissue.

Systems which operate in the near field (Fresnel zone) include ultrasound divices for physical therapy applications. These systems typically feature large surface area contact transducers which are intended to develop deep heat in damaged tissues, as compared to mechanical (non thermal) effects.

Currently, no systems exist for distributing a uniform wide beam of ultrasound for a mechanical (substantially non thermal) effect over a large volume of tissue, in a short period of time, so as to promote uniform cellular uptake of drugs and/or to uniformly enhance transfection of DNA over a large tissue volume. Such transcutaneous uniform acoustic intensity would need to be sufficiently powerful so as to cause acceptable cellular absorption and/or transfection yet sufficiently weak to prevent cell lysis or DNA fractionation. More specifically, no system exists for applying a uniform dose of therapeutic ultrasound, in a timely manner, over an area of a spreading injectate bolus.

SUMMARY OF THE INVENTION

The present invention provides systems, methods and kits for delivering a uniform field of ultrasound energy over a wide target region of a patient's body. The present invention offers the advantages of enhancing cellular absorption and/ or transfection of therapeutic substances delivered by injection into a patient's body. In another aspect, the present invention is also useful for the treatment of vascular structures at risk from intimal hyperplasia.

Co-pending applications Ser. No. 09/364,616, Ser. No. 09/255,290, and Ser. No. 09/126,011, describe systems for ultrasound enhancement of drug injection.

The present invention provides a variety of wide beam ultrasound delivery systems which have the advantage of delivering therapeutic ultrasound energy over a large tissue volume such that, in preferred aspects, ultrasound energy can be uniformly distributed over the region in which a therapeutic substance has been injected intramuscularly, in a short time frame as compared to the lifetime of the substance at the site of interest. An advantage of the present invention is that by applying a uniform field of ultrasound energy over a large tissue volume, cellular uptake of injected substances such as therapeutic DNA can be substantially enhanced over the entire region in which the injected DNA spreads without inflicting tissue damage or degrading the injectate. Another advantage of the present invention is that by applying a uniform field of ultrasound energy over a long length of vascular structure, a healing response might be invoked to blunt excessive growth of intimal hyperplasia without adjacent tissue damage.

An advantage of the present invention is that it provides systems for both delivering wide ultrasound beams and for scanning ultrasound beams. As such, the present invention is particularly well adapted to operate under both conditions in which time constraints are present and conditions under which time constraints are not present, as follows.

If time constraints exist, therapeutic applications requiring continuous wave (CW) exposure by ultrasound will require devices which have fields of view larger than the insonication area of interest. If there is no time limit such as that limit imposed by the natural degradation of DNA within the body, devices with smaller fields of view may be swept or stepped over the insonication area of interest.

Again, if time constraints exist, therapeutic applications which operate with pulse wave (PW) exposure by ultrasound may also require devices which have fields of view larger than the insonication area of interest if the ultrasound beam cannot be shifted away from a first sonication site during the OFF time to a second (or third, or fourth, . . . ) sonication site for the ON time of that second (or third, or fourth, . . . ) site. For applications with very small duty cycles, where duty cycle is defined as the ratio of the ON time divided by the ON and OFF time, the ultrasound beam may be swept across a multitude of alternative sites, the net effect being a similar amount of ultrasound exposure (uniform exposure) to all points within the subject area of interest.

In preferred aspects, the present wide beam ultrasound delivery system comprises a housing having an opening at its distal end with an ultrasound transducer suspended within the housing. The ultrasound transducer is positioned in contact with an acoustic couplant material which substantially fills the housing. In preferred aspects, the acoustic couplant material is a fluid such as water, water with additives such as wetting agents and/or anti biological agents (to prevent build up of bacteria or fungus), or oils.

A flexible skin-contact window, which may be made from any of several variations of silicone rubber, polyethylene, polypropylene, nylons, urethanes and the like, is disposed across the opening at the distal end of the housing. The skin-contact window is preferably positioned adjacent to the patient's skin with possibly an ultrasonic coupling gel between the window and skin such that therapeutic ultrasound energy can be conducted from the ultrasound transducer along through the fluid-filled housing and then through the skin-contact window and into the patient.

In preferred aspects of the present invention, the housing of the ultrasound delivery system is designed to assure good coupling of ultrasonic energy to the external configuration of the patient. Additionally the housing preferably contains adequate ultrasonic absorbing materials such that ultrasonic energy does not propagate to the external surface of the housing thus sonicating the operator of the equipment. Furthermore, the housing preferably is designed such that it does not interfere with the ultrasonic beam in the form of unintended ultrasonic beam stops.

In various aspects, the piezoelectric element of the ultrasound transducer is generally planar and may either be rectangular, circular, or annular in shape. In particular embodiments, the transducer may comprise a plurality of annular-shaped piezoelectric elements disposed concentrically, one within another. Alternatively, the transducer may comprise piezoelectric elements which are generally cylindrical in shape. In further embodiments, the transducer may comprise single or multiple element three dimensional piezoelectric shapes. Yet further, the transducer may comprise a two-dimensional array of individual flat-plate piezoelectric elements. The transducer elements of the present invention preferably have a large surface area ranging, in preferred aspects, from typically 0.5 $cm^2$ to 1000 $cm^2$.

It is understood that the shape of the piezoelectric element of the transducer in association with any and all focussing elements will effect the shape of the ultrasonic footprint in tissue, defined as the area of therapeutically effective ultrasound. Some applications of the present systems may preferably use circular footprints while others may preferably use rectangular shapes. By way of example, an unfocussed rectangular transducer might produce a rectangular footprint with the long axis of the transducer being orthogonal to the long axis of the footprint.

In preferred aspects, the present invention also comprises various systems for directing the ultrasound energy through the fluid filled housing to targeted depths in the patient's body. Such systems may optionally comprise curving the piezoelectric ceramic to shape the beam width. Alternately, lens structures may be attached to the front emission surface of the piezoelectric ceramic to effect the same. Further, reflective surfaces may be installed in the housing so as to achieve the same. And yet furthermore, refractive acoustic lenses may be placed in the acoustic beam in the fluid couplant medium to shape the beam width.

In preferred aspects, the back surface of the piezoelectric ceramic is covered with air to assure the emission of all acoustic energy out the front surface of the same. Consequently thermal dissipation corresponding energy backward radiated in the device will be substantially reduced and maximal efficiency achieved. Alternately, the back surface of the ceramic may instead be covered with low impedance lightly attenuating materials to provide some level of structural strength to the device. Preferably, the edges of the piezoelectric ceramic are mounted within the housing so as to minimize acoustic coupling to the housing.

In alternative aspects of the invention, first and second mounting systems are provided for connecting the transducer to the interior of the housing such that the transducer can be articulated for controllable back-and-forth scanning movement of a beam of ultrasound energy. Preferably, by moving the transducer back-and-forth in two perpendicular directions, a narrower beam of ultrasound energy can be raster scanned across the desired volume of tissue in the patient and over time achieve uniform illumination of subject tissues.

The present invention is particularly well suited for (although not constrained to) use in conjunction with intramuscular injections of therapeutic substances such as DNA. In such aspects, the present wide aperture ultrasound delivery system can be used either before, concurrently with, immediately after, or substantially after the injection of a therapeutic substance into the patient. As defined herein, application of ultrasound "substantially after" injection comprises application of ultrasound in the period of time before which the injected DNA has been substantially degraded. Typically, such a time period will be on the order of 15 to 60 mins., but is not so limited and may vary from one application to another.

As such, the present invention is ideally suited for enhancing cellular absorption of a drug or any other substance into a local target region of a patient's body, thereby avoiding the undesirable effects of the substance being widely dispersed throughout the patient's body by the patient's cardiovascular system.

For example, specific applications of the present invention include the application of sonicated VEGF therapy for the treatment of ischemic tissues as described above. Further applications include the treatment of patients suffering from diseases as a result of specific protein deficiencies. Specifically, such patients may be helped by the injection of specific DNA plasmids to stimulate cells to secrete these proteins, such as EPO for patients with impaired production of red blood cells, Factor VIII or Factor IX for hemophiliac patients, or angiostatin or endostatin for cancer patients.

The present system's advantageous applications of a uniform wide beam ultrasound exposure are not limited to those in conjunction with substance injection. For example, the present invention is also particularly well suited for use in the prevention of intimal hyperplasia in conjunction either before, concurrently with, immediately after, or substantially after vascular intervention or surgery. As such, a further advantageous application of the present invention is its ability to distribute a uniform wide beam of ultrasound for a mechanical (non thermal) effect to evoke a vascular healing response along an extended portion of artery or vein.

It has been demonstrated that vascular tissues at risk of intimal hyperplasia, such as coronary or peripheral arteries following vascular intervention or veins and arteries following graft insertion or the creation of a fistula, experience a reduced hyperplasia burden if treated with ultrasound immediately following injury. In the case of vascular intervention with devices such as angioplasty balloons, arthrectomy catheters, or stents, the extent of vascular injury might range from a few millimeters in length to several centimeters or more in length.

Co-pending applications Ser. No. 09/223,230, and Ser. No. 09/345,661, describe catheter based systems for delivering a field of ultrasound to a region of tissue.

In addition to encompassing systems for delivering a wide field of uniform ultrasound to the surface of a patient's skin, the present invention also encompasses wide beam aperture systems for delivering a wide field of uniform ultrasound to a region of tissue to inhibit intimal hyperplasia in the vascular system.

In accordance with the present invention, patients receive a wide field of uniform ultrasound exposure from external sources either during the initial vascular intervention or some period thereafter. Such transcutaneous uniform acoustic intensity is preferably of a sufficient power so as to excite the healing response yet is not excessively strong to evoke an inflammatory response or to lyse blood or tissue cells.

The present invention is not limited as to the nature of the cells which compose the target site. Such cells may be muscle or organ cells receiving transcutaneous, intraoperative, or percutaneous injection. Such cells may include vascular cells.

DESCRIPTION OF THE SPECIFIC EMBODIMENTS

Figure 1:
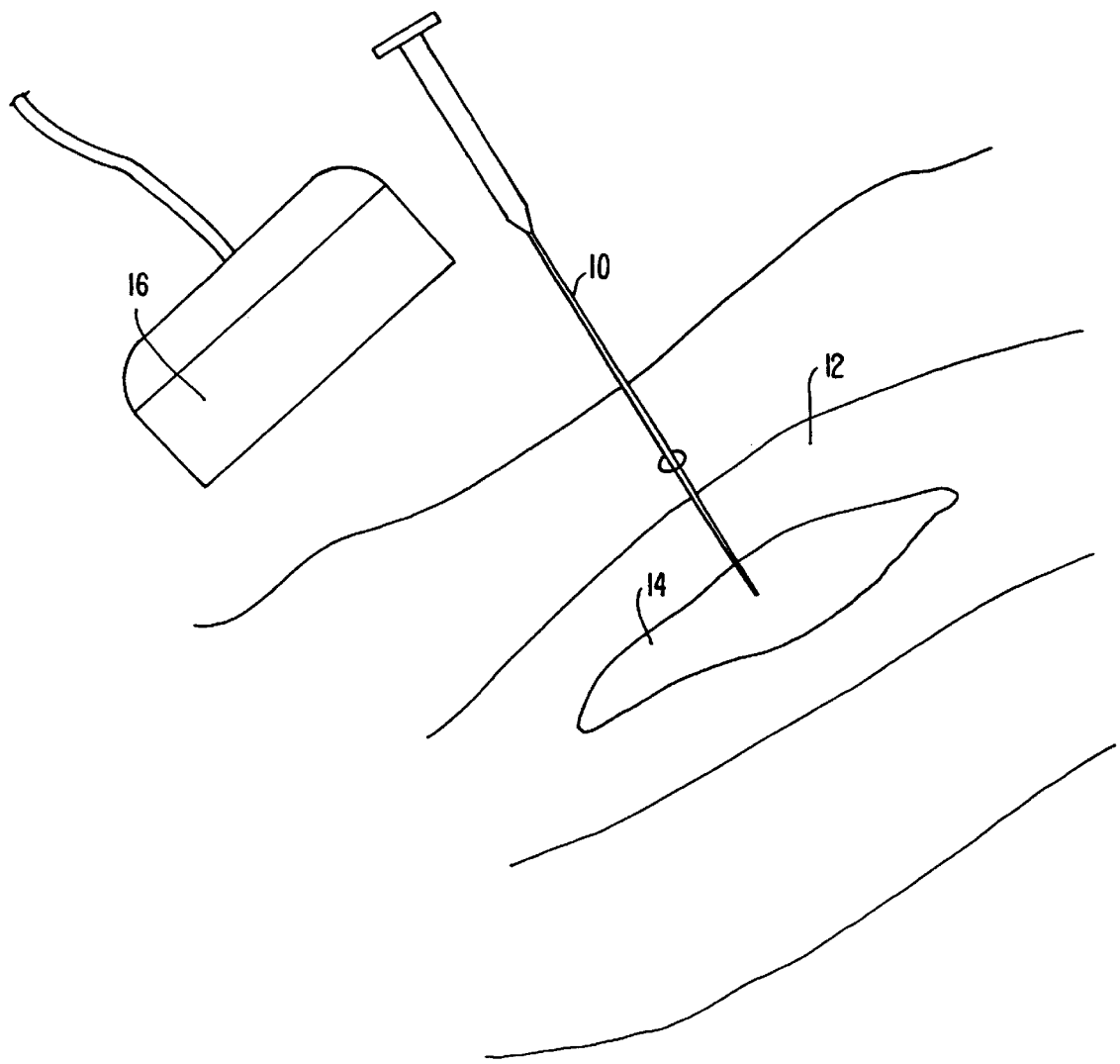
FIG. 1 illustrates an ultrasound system enhancing transfection of injected substance in skeletal muscle.

The present invention provides a variety of wide beam ultrasound delivery systems which have the advantage of being able to deliver a uniform exposure of therapeutic ultrasound energy over a much larger volume of tissue than previous systems. An advantage of such a wide beam delivery is that therapeutic ultrasound can be delivered across an entire target region into which a drug, DNA, or other therapeutic substance has been injected. Accordingly, the present invention can be used to promote the cellular uptake of the drug, DNA, or other therapeutic substance prior to, concurrently with, immediately after, or substantially after its injection as the drug, DNA, or other therapeutic substance disperses through a region of a patient's musculature or organ.

These properties of the present invention are particularly advantageous since a therapeutic injection of DNA into a human patient will typically diffuse into the patient's musculature. In particular, ultrasonic imaging has demonstrated that an injection bolus typically follows muscle fibers and may spread across a length of five or more centimeters parallel to the muscle fiber and perhaps over a width of one to two centimeters normal to the muscle fibers.

Yet another advantage of the present invention is that a uniform dose of therapeutic ultrasound can be delivered to an extended section of vascular tissues at risk of intimal hyperplasia, such as coronary or peripheral arteries following vascular intervention or veins and arteries following graft insertion or the creation of a fistula. As such, the present invention can be used to minimize intimal hyperplasia.

Yet another advantage of present invention is that the bio-effects of the ultrasonic energy delivered by this invention are primarily mechanical in nature (cavitational, pressure, or high frequency vibration) with minimal thermal contribution (heat due to absorption of energy or energy conversion). As such, unwanted tissue heating is avoided.

The American Institute for Ultrasound in Medicine (AIUM) and the National Electrical Manufacturers Association (NEMA) in "Standard for Real-Time Display of Thermal and Mechanical Indicies on Diagnostic Ultrasound Equipment", 1991, have together defined the terms "mechanical index" MI and "thermal index" TI for medical diagnostic ultrasound systems operating in the frequency range of 1 to 10 MHz. Although therapeutic ultrasound is not included within the scope of this standard, the terms are useful in characterizing ultrasound exposure.

The mechanical index is defined as the peak rarefactional pressure $P_-$ (in MPa) at the point of effectivity (corrected for attenuation along the beam path) in the tissue divided by the square root of the frequency F (in MHz), or $$MI = P_-[MPa]/sqrt(F[MHz])$$

The tolerated range for medical diagnostic equipment is up to an MI of 1.9. MI values above approximately unity represent acoustic levels which can cause mechanical bio-effects in human subjects.

The thermal index is defined as the average energy W (in mW) times the frequency F (in MHz), divided by the constant 210, or $$TI = W[mW] * F[MHz]/210$$

A TI of 1 implies a temperature increase in normally vascularized muscle tissue of one Centigrade degree. The FDA standard for a maximum temperature of surface contact ultrasound devices is 41 degrees C. "Deep heat" ultrasound therapy devices may generate higher temperatures within tissue. In the vascular arena, however, even slight temperature excursions may cause unwanted formation and accumulation of clot. Moreover, increased temperature of tissue may cause inflammation in the area of treatment. Therefore, TI values in excess of four are generally considered the threshold for causing undesirable bio-effects.

TI values greater than four may be calculated in accordance with the techniques described above. The TI parameter as defined represents a steady state condition, not a short term "transient" exposure. Using the assumption of 0.3 dB/MHz/cm as the energy absorption rate for normally vascularized muscle tissue, adequate doses of ultrasound can be delivered to achieve enhanced cellular absorption and/or transfection before thermal energy within the tissues generates an unacceptable temperature. Due to the difference in total energy absorption between the transient and continuous exposure, the AIUM definition of TI used herein refers to the continuous TI, as compared to the transient TI.

In accordance with the present invention, ultrasound energy is applied with a transient TI of less than 4, and more preferably less than 2, and most preferably less than 1.

As will be explained, the present invention provides systems and devices for delivering a uniform wide beam of ultrasound energy across a rather large volume of tissue. As such, a uniform therapeutic effect can be achieved over the desired region of tissue in a timely manner.

FIG. 1 illustrates an exemplary aspect of the present invention, in which DNA is injected by needle 10 into a patient's leg musculature 12. As stated above, the injected DNA will quickly diffuse across a section of muscle tissue, region 14. Subsequent to injection, an ultrasound transducer 16 is placed into contact with the tissue to promote DNA uptake by directing an ultrasound field toward region 14.

Figure 2:
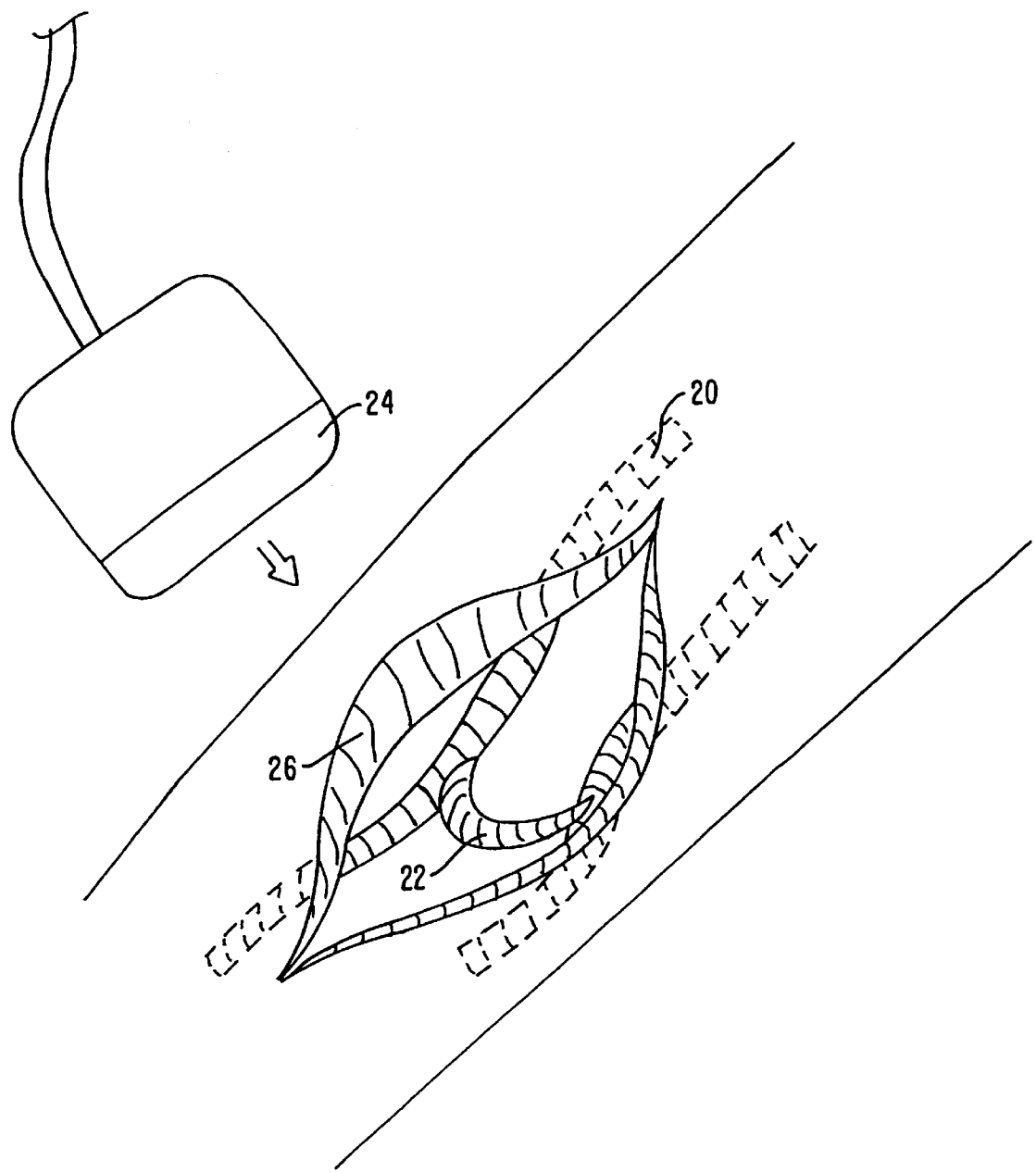
FIG. 2 illustrates an ultrasound system treating vascular sections following surgery.

FIG. 2 illustrates another exemplary aspect of the present invention, in which ultrasonic therapy alone is directed to the venous side 20 of an artero-venous (A–V) graft 22 in a patients arm. An ultrasound transducer 24 with a wide field of view is placed either in the surgical incision 26 and coupled with sterile fluid such as saline or is placed over the skin post surgery (not shown). Equivalently (but not depicted), an ultrasonic transducer can be placed into a surgical incision for therapy after fistula creation or on the patient's skin for post surgical procedure vascular therapy.

Figure 3:
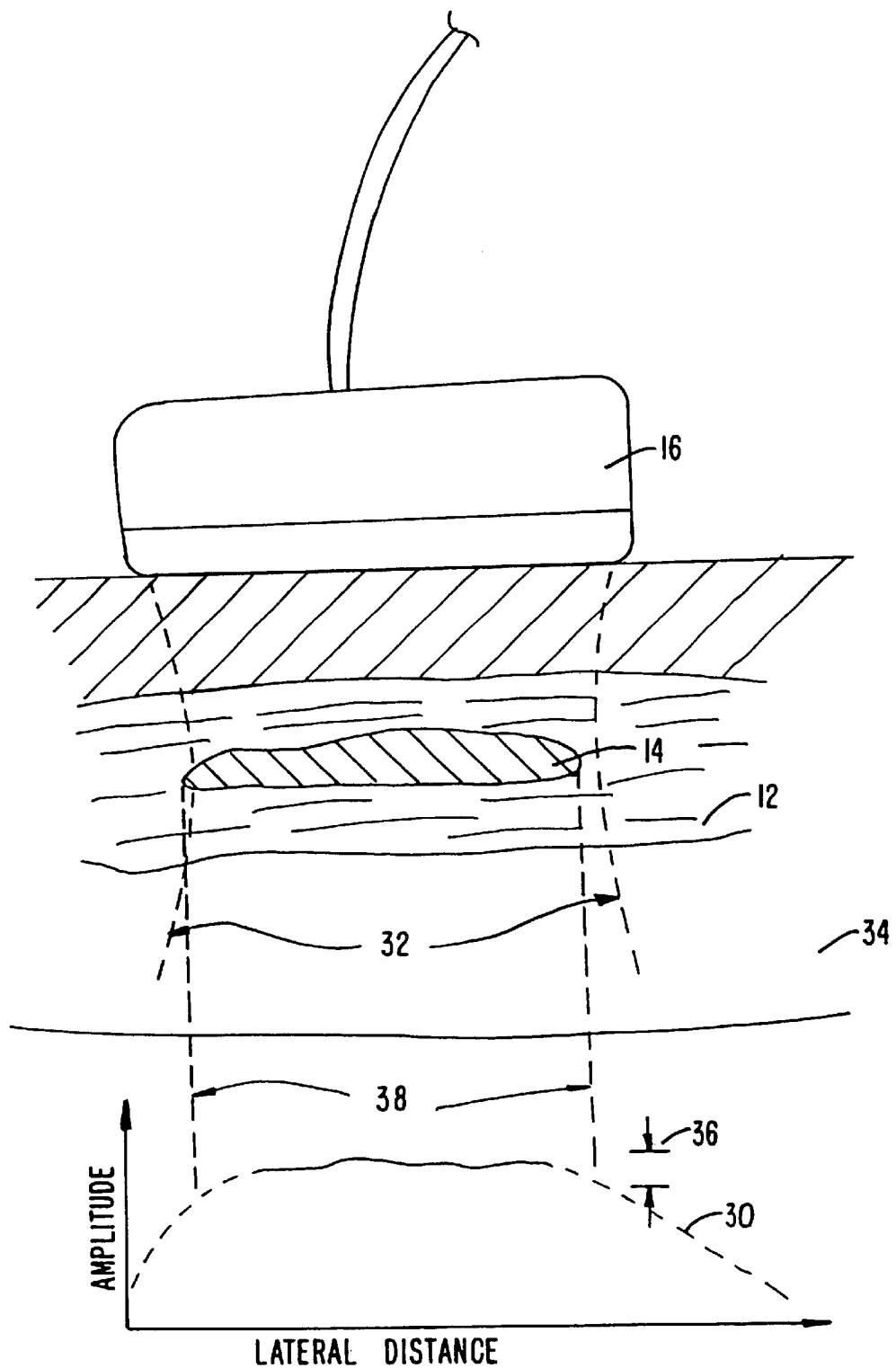
FIG. 3 illustrates a preferred lateral beam profile superimposed upon a target region in a patient's body.
Figure 4:
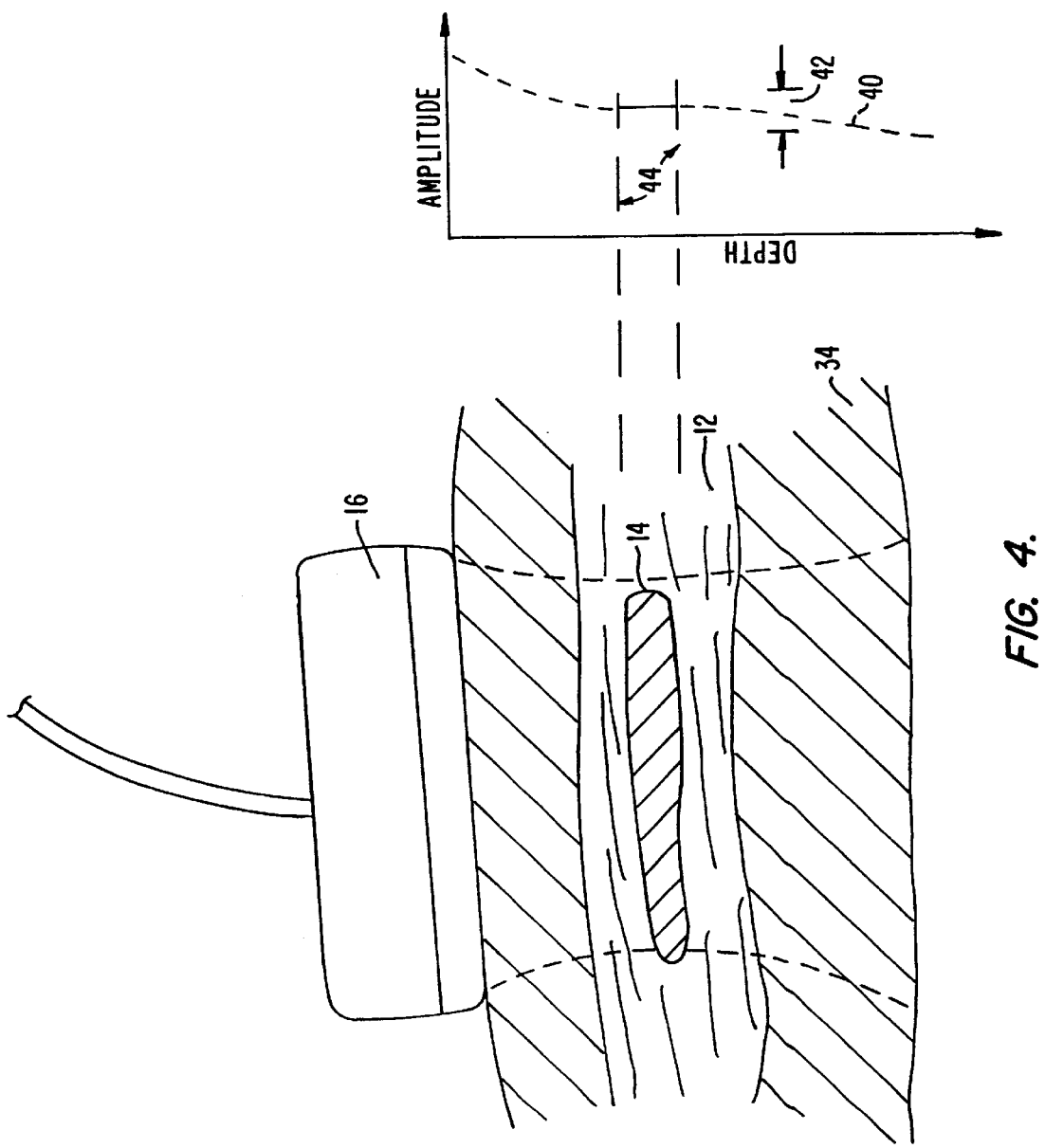
FIG. 4 illustrates a preferred axial beam profile superimposed upon a target region in a patient's body.

In preferred aspects of the present invention, the ultrasound field will be uniform across the two orthogonal directions of the sample tissue and through its depth. FIG. 3 depicts the lateral profile 30 of a preferred ultrasonic beam 32 of the wide field transducer 16 superimposed over the region 14 of substance diffusion in the muscle 12 of a patient's leg 34. In preferred aspects of the present invention, the acoustic amplitude will be uniform within prescribed limits 36 over the region of interest 38. Outside of this region of interest, the acoustic amplitude may fall off in any manner. FIG. 4 depicts the axial beam profile 40 for the same clinical configuration as in FIG. 3. In preferred aspects of the present invention, the acoustic amplitude will again be uniform within prescribed limits 42 through the depth 44 of tissue 14 containing the injected substance. Again, proximal or distal to the region of interest, the acoustic beam may take any other amplitude provided bio-effects remain within acceptable limits.

Preferred and exemplary prescribed limits 36 and 42 for the uniformity of the ultrasound beam field will be within plus/minus 5 dB across its width, or across the width of the target region if an ultrasonic beam is scanned across a target region, as will be described. More preferably, the uniformity will be within plus/minus 3 dB, and most preferably within plus/minus 1.5 dB.

The area of the target region in the human body will vary with the application. For gene therapy, for example, the area of the ultrasound beam field will be at least 0.5 cm2, and more preferably, at least 1.0 cm2, and most preferably, at least 10 cm2.

Figure 5:
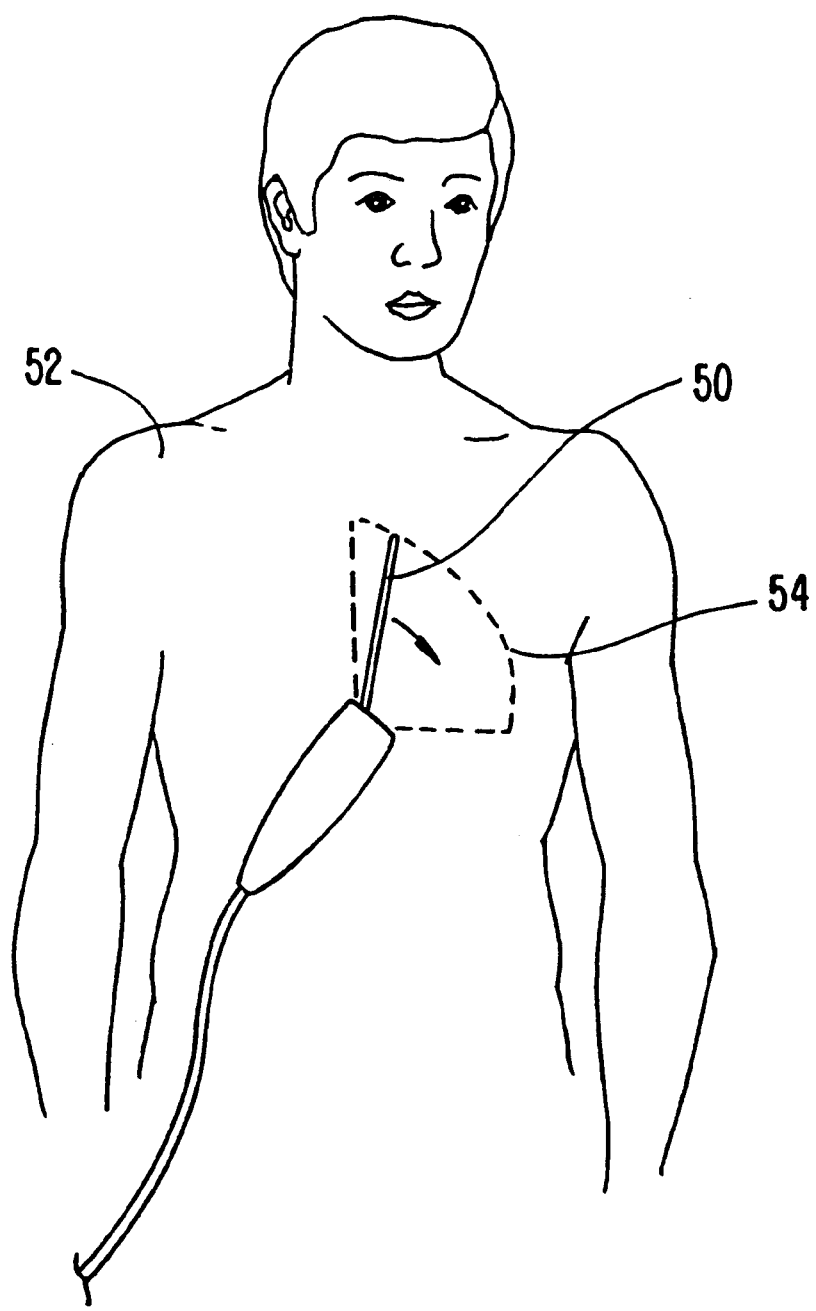
FIG. 5 illustrates conventional medical diagnostic ultrasound imaging of the human body.

As depicted in FIG. 5, current medical diagnostic ultrasound imaging and Doppler systems are designed to electronically or mechanically scan a highly focused beam 50 of higher frequency (typically 2 to 30 MHz) ultrasound through a patient's body 52, with lateral beam widths in the range from typically one millimeter to one hundred microns. Short transmit bursts with on the order of one to three cycles provide best axial resolutions. Peak amplitudes are limited to that energy just sufficient to create images out to the point of degrading resolution. While these systems deliver an effectively uniform dose of ultrasound energy over the width of the scan plane 54, the scan planes 54 are typically narrow and one dimensional, frequencies are generally too high for a predominantly mechanical effect in tissue, peak amplitudes are insufficient for a biological effect, and duty cycle at any one location is far below that required for a biological effect.

Figure 6A:
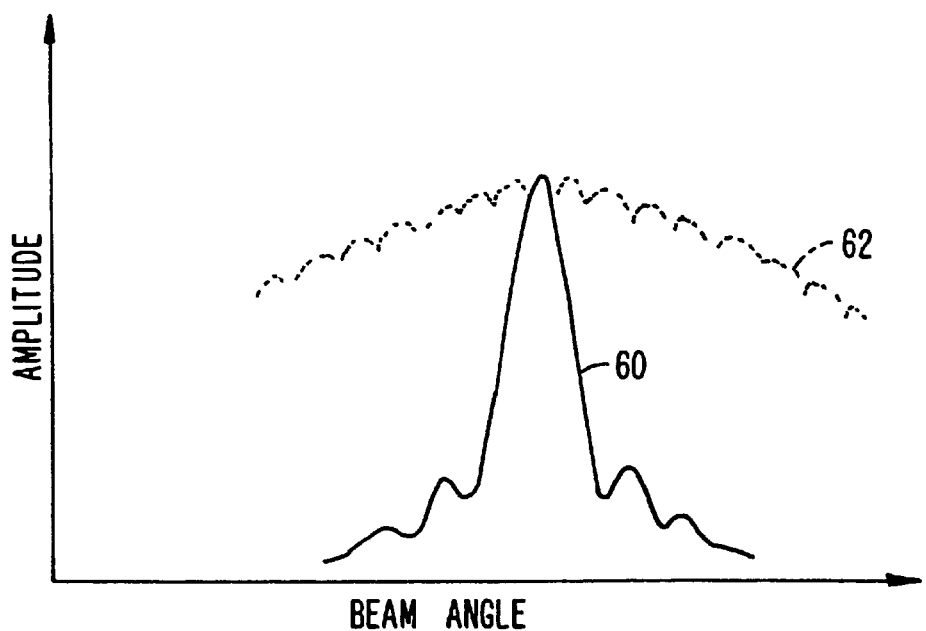
FIG. 6A illustrates a lateral in-plane beam profile from a medical diagnostic imaging system.
Figure 6B:
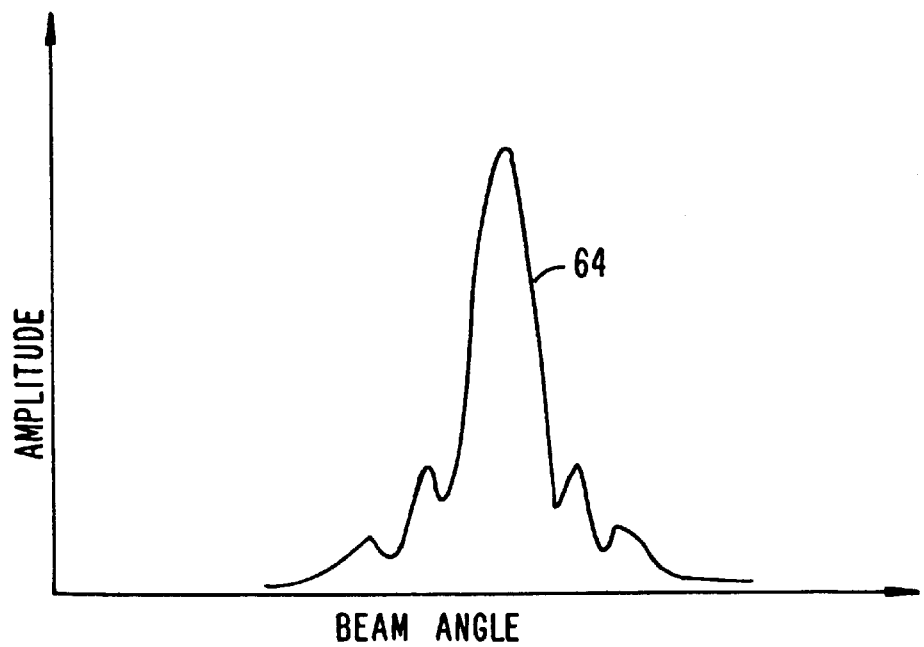
FIG. 6B illustrates a lateral cross-plane beam profile from a medical diagnostic imaging system.
Figure 7:
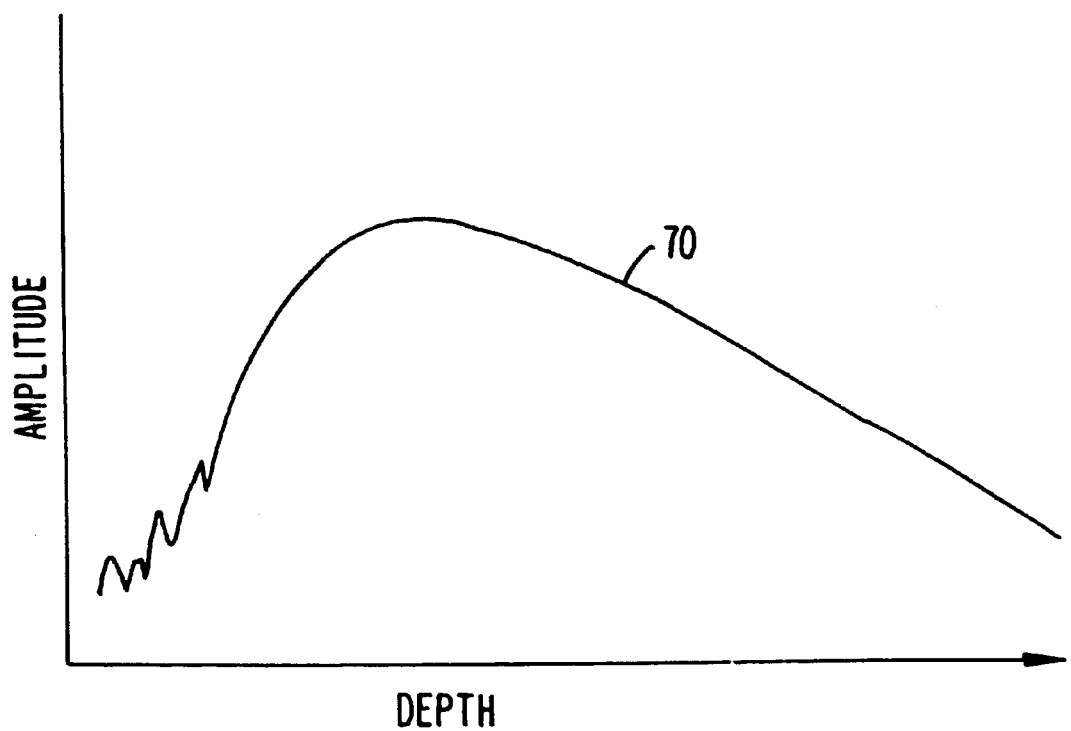
FIG. 7 illustrates axial beam profiles from a medical diagnostic imaging system.

More specifically, FIG. 6A depicts the lateral beam profile 60 from a typical diagnostic ultrasound imaging system. These profiles are quite narrow down to typically 30 to 50 dB from peak amplitude and thence broaden substantially. Across the scan plane, mechanically swept systems typically maintain the same peak amplitude as a function of angle while the phased array systems might typically see a 6 to 12 dB variation in amplitude 62, as depicted in FIG. 6A. In the cross plan (orthogonal to the scan plane), the beam exhibits a very narrow profile 64 as depicted in FIG. 6B. FIG. 7 depicts the axial profile 70, the signal strength down the central axis of the transducer. Near the focal zone, the beam achieves peak amplitude, which is relatively uniform over a moderate depth.

Figure 8:
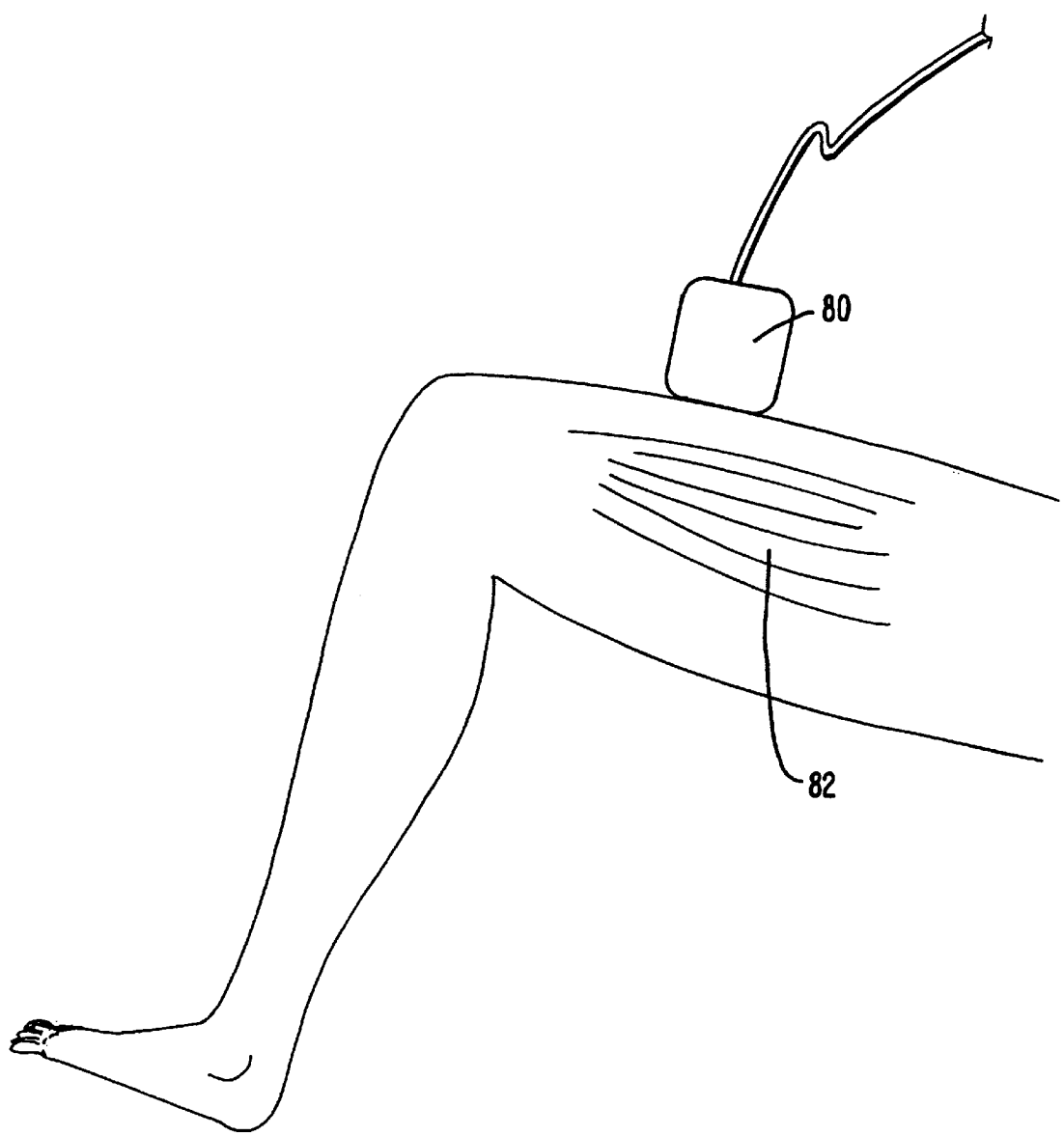
FIG. 8 illustrates the application of therapeutic ultrasound for "deep heat" treatment of human muscles.
Figure 9:
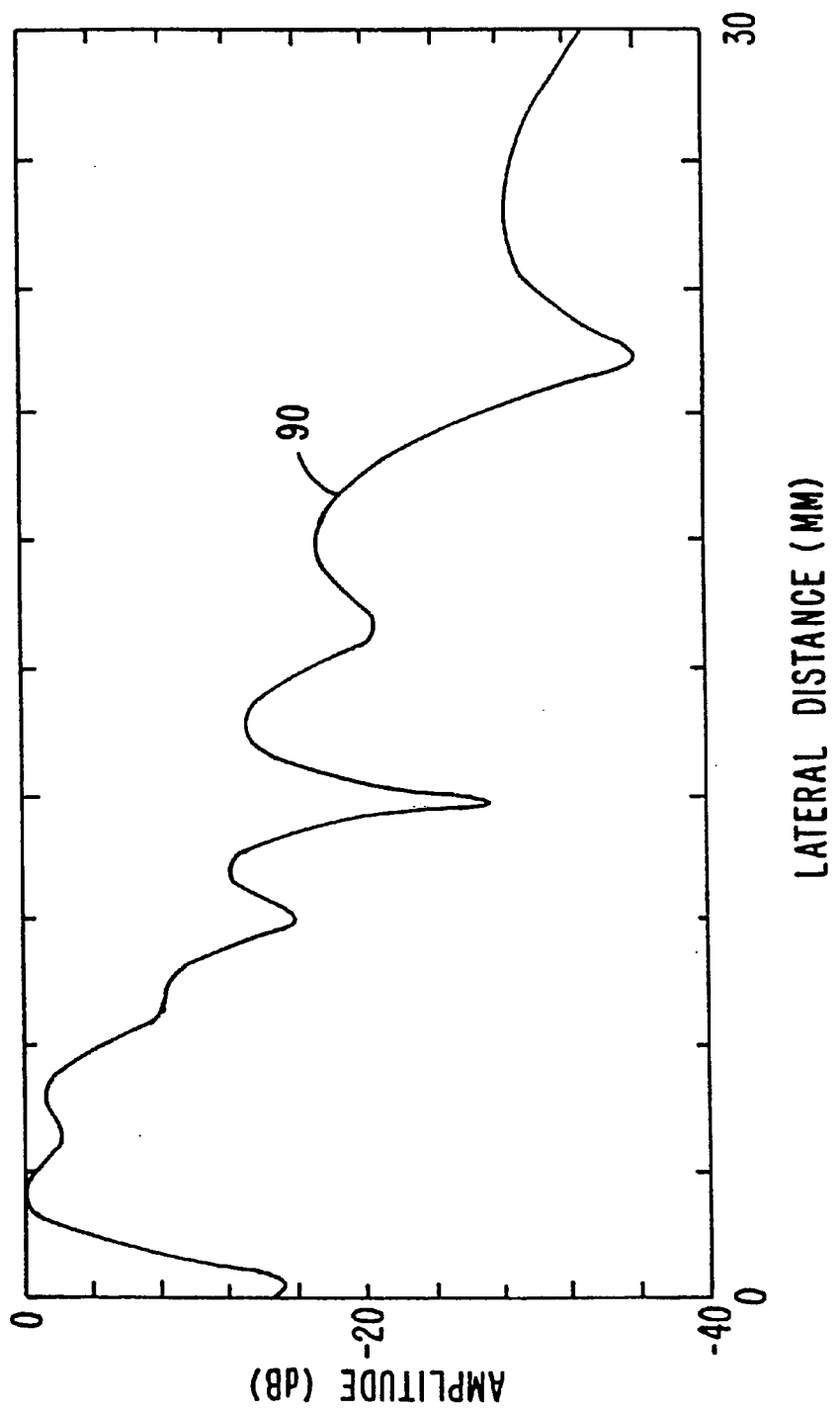
FIG. 9 illustrates a modeled lateral beam profile from a typical physical therapy ultrasound system.
Figure 10:
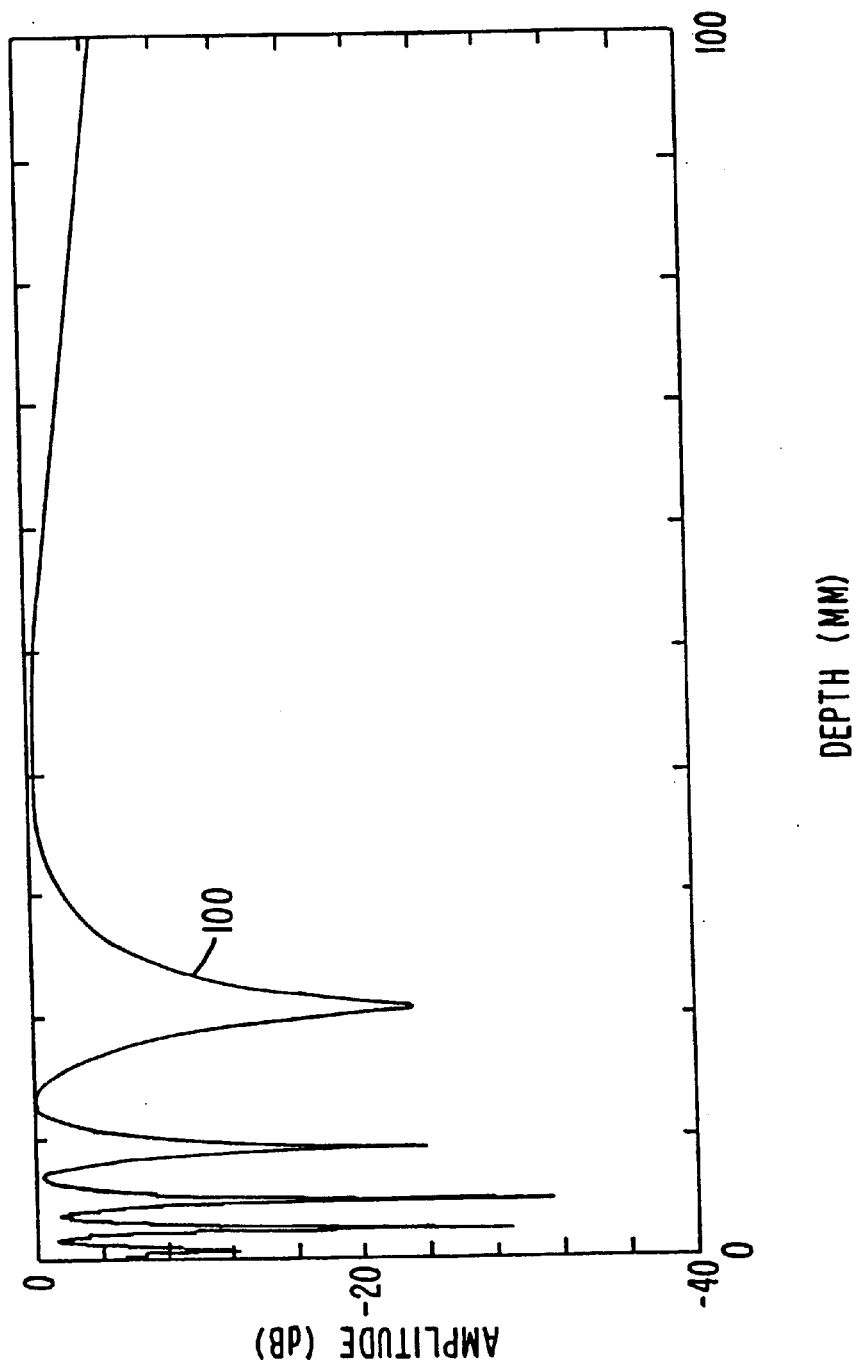
FIG. 10 illustrates a modeled axial beam profile from a typical physical therapy ultrasound system.

Transducers 80 for physical therapy as depicted in FIG. 8 are typically employed to develop deep heat in injured muscles 82. These devices are typically single element, unfocused transducers. Due to operation in the near field, these devices exhibit highly irregular ultrasonic intensities both as a function of depth and as a function of lateral position. Indeed, FIG. 9 depicts a modeled lateral profile 90 of a 16 millimeter diameter, 1 MHz, unfocused transducer at a distance of twenty millimeters from the surface. Across the aperture of the device, the variation of signal strength exceeds 15 dB. From the surface of the transducer to the focal distance, the shape of the lateral profile also varies radically with depth. FIG. 10 depicts a modeled axial profile 100 (ultrasonic intensity along the central axis of the transducer) for the same device. The ultrasonic intensity in the first 30 millimeters, corresponding to patient tissues directly in contact with and under the device, is seen to vary through a 20 dB range. A variation of the physical therapy system for laboratory experimentation is the Sonoporator 100, made by ImaRx corporation of Tucson, Ariz., which delivers a maximum 2 W/cm2 (MI=0.25) of ultrasound from a 16 millimeter diameter transducer, in the 1 MHz frequency range. This type of device is expected to deliver beam profiles as stated above.

High intensity focused ultrasound (HIFU) systems typically employ single element focused transducers which deliver beam profiles similar to those of diagnostic imaging systems. These transducers are thence swept over the surface of the patient to develop thermal lesions at the focal depth. The higher frequencies have minimal mechanical bio-effects.

The present invention exceeds the performance of the current existing ultrasound systems depicted in each of FIGS. 6, 7, 8, 9, and 10, by instead exhibiting a uniform ultrasound field over a wide area as depicted in FIGS. 3 and 4.

Figure 11:
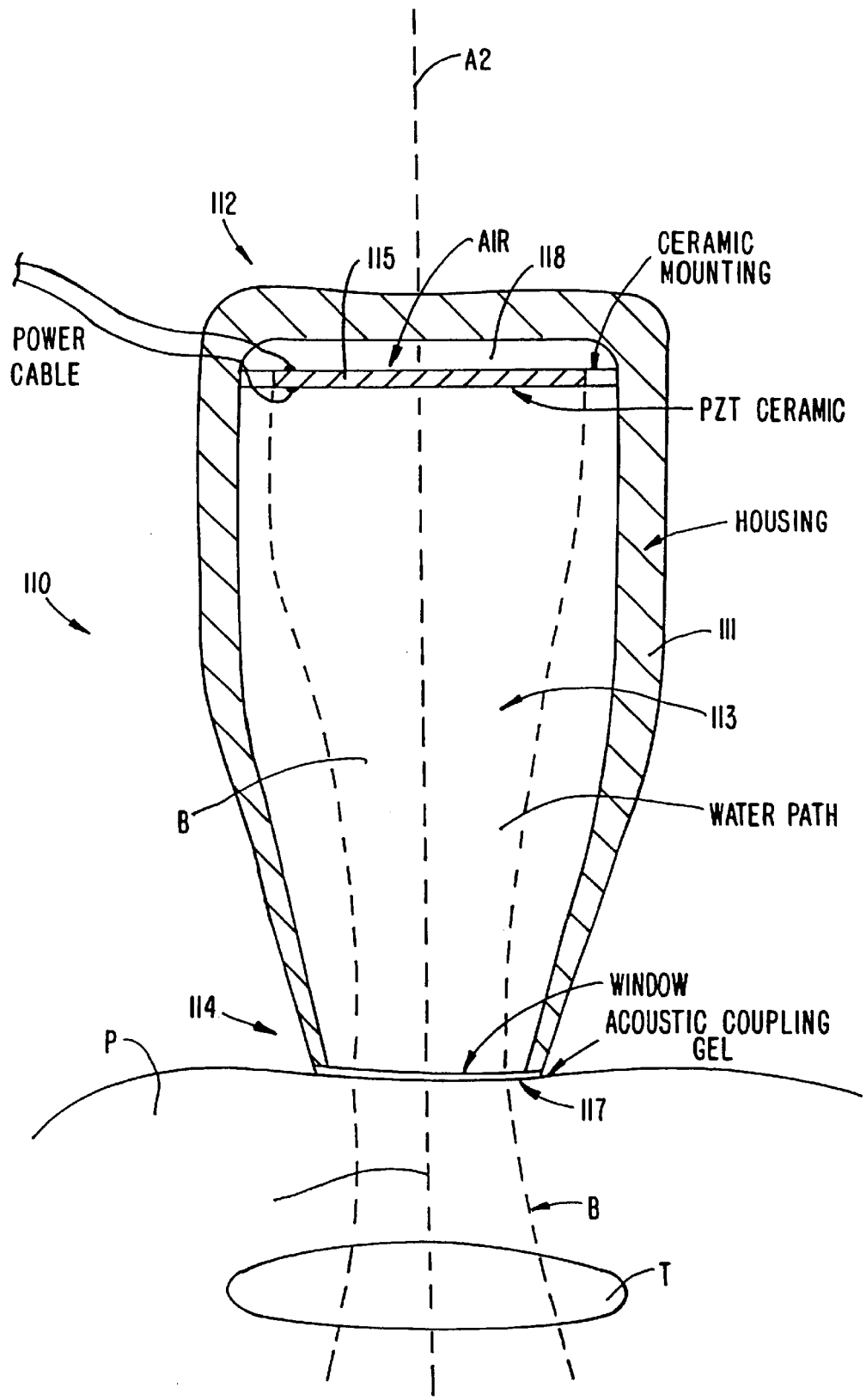
FIG. 11 is a sectional side elevation view of a first embodiment of the present wide aperture beam delivery system.

FIG. 11 is a sectional side elevation view of a first embodiment of the present wide beam uniform exposure ultrasound delivery system. Ultrasound delivery system 110 comprises a housing 111 having a proximal end 112 and a distal end 114. An ultrasound transducer 115 is disposed at the proximal end 112 of housing 111 as shown. Housing 111 may preferably be generally cylindrical in shape and may be tapered to a narrow distal end 114, as shown. Distal end 114 of housing 111 is preferably covered with a flexible skin-contact window 117 which may be supported against the skin of patient P. Preferably, a standard acoustic coupling gel is applied between window 117 and the skin of patient P, to facilitate the transmission of therapeutic ultrasound energy to the patient.

Housing 111 is preferably filled with an acoustically couplant material 113, which may preferably comprise a fluid such as water with or without additives or oil. Fluid 113 operates to conduct the beam of ultrasound energy there-through from transducer 115 to skin-contact window 117.

In one aspect, transducer 115 may preferably be flat and circular in shape, as shown. In preferred aspects, the diameter of transducer 115 may be in the range of 10 mm to 100 mm, yielding a surface area of 0.8 $cm^2$ to 80 $cm^2$.

Transducer 115 may be made of a piezoelectric ceramic material, for example, a PZT ceramic, or more specifically, a PZT-8 ceramic, or other variation of a hard piezoelectric ceramic optimized for high power operation. PZT-8 ceramic materials or equivalents are available from most vendors of piezoelectric ceramic, such as Morgan Matroc, Inc., of Cleveland, Ohio. Alternatively, the transducers might be fabricated from single crystal piezoelectrics, such as those manufactured by Stratum Technologies, Inc., of State College, Pa. In addition, the present piezoelectric materials are not limited, but may alternatively be made from families of materials including lithium niobates, lead titonates, lead metaniobates, various composites, and any other suitable materials. Furthermore, variations on the transducer design may also include using magnetostrictive materials as the ultrasonic driver elements.

Transducer 115 is shown in FIG. 11 to be in direct contact with the fluid path medium 113. If it is necessary to electrically insulate the transducer from the fluid medium, the transducer may be coated with an insulating material, such as a Humiseal 1B31 acrylic manufactured by the Chase Corp. of Woodside, N.Y. Alternatively, the front surface of the transducer may feature one or more impedance matching layers, for purposes of wave form shaping, mechanical strength, or again, electrical insulation. In the case of a single impedance matching layer, a quarter wave length thickness of a 3103 casting epoxy manufactured by Tra-Con of Bedford, Mass. is desirable. Ideally, the impedance matching layers will present with minimal acoustic attenuation, as any absorbed energy will heat the delivery device.

An air pocket 118 may be provided on the back side of transducer 115 such that substantially all of the ultrasound energy emitted by transducer 115 is then directed distally through fluid 113 toward skin-contact window 117 at distal end 114 of housing 111. The air-ceramic interface on the back side of the transducer provides an excellent reflector of acoustic energy back to the distal direction. Air is further-more an extremely poor conductor of ultrasound energy. Alternatively, a low impedance acoustic material with a low acoustic attenuation may be utilized for purposes of mechanical strength in the device.

Preferably, the structural side walls 111 of the delivery device housing are ideally coated with anti reflective, highly absorptive material, such as heavily loaded silicone rubbers. As such, side lobe energy from the transducer within the housing would not be allowed to scatter so as to interfere with the primary acoustic beam.

Preferably, the physical size of the delivery device opening at the distal end will be fabricated such that the effect of a beam stop on the primary ultrasound beam will be a constructive/destructive ripple pattern with an amplitude fluctuation well within the uniformity specification of the device. (IE: within the preferred ranges of uniform ultrasound exposure, as set forth herein).

Figure 12A:
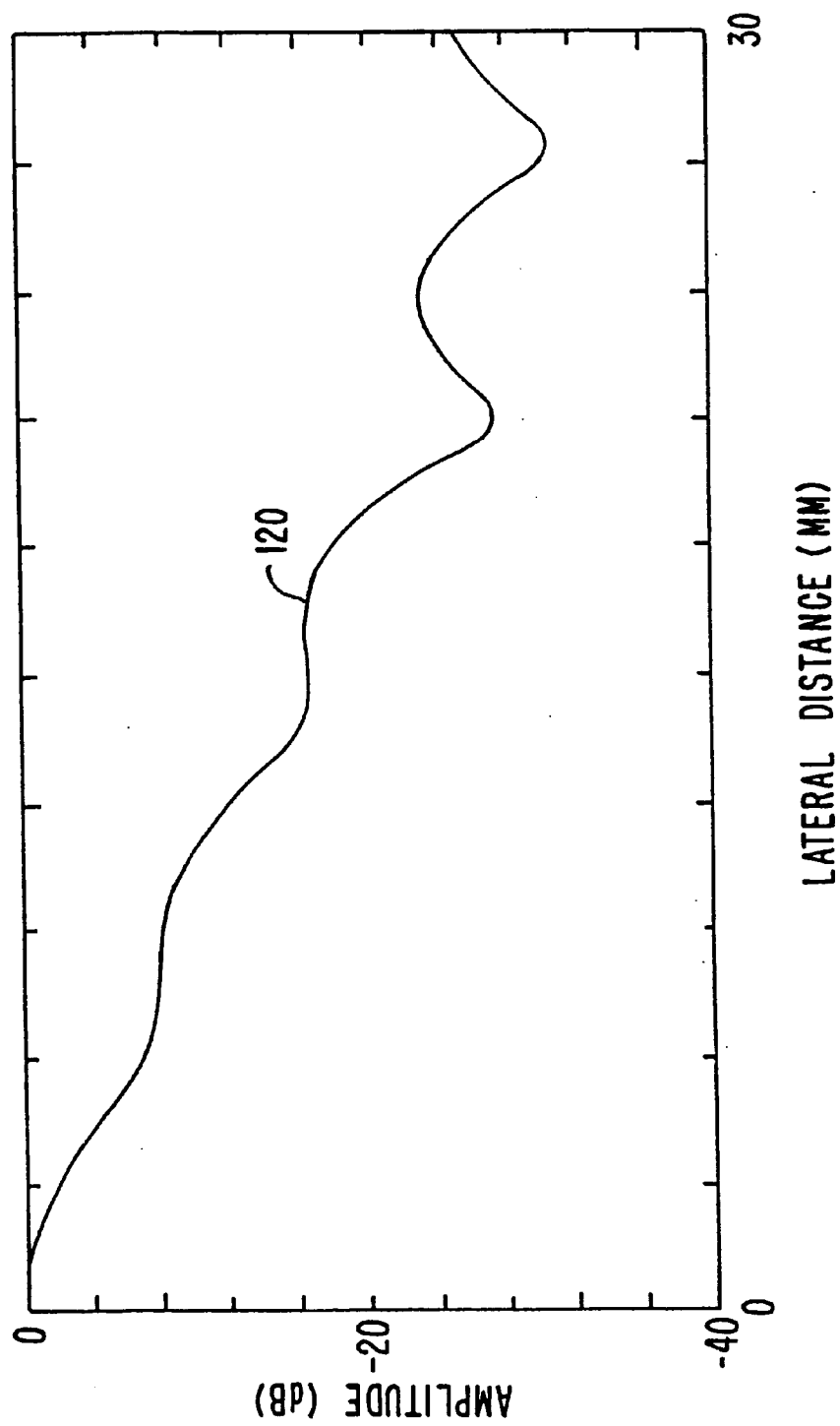
FIG. 12A illustrates a modeled lateral beam profile of the transducer of FIG. 11.
Figure 12B:
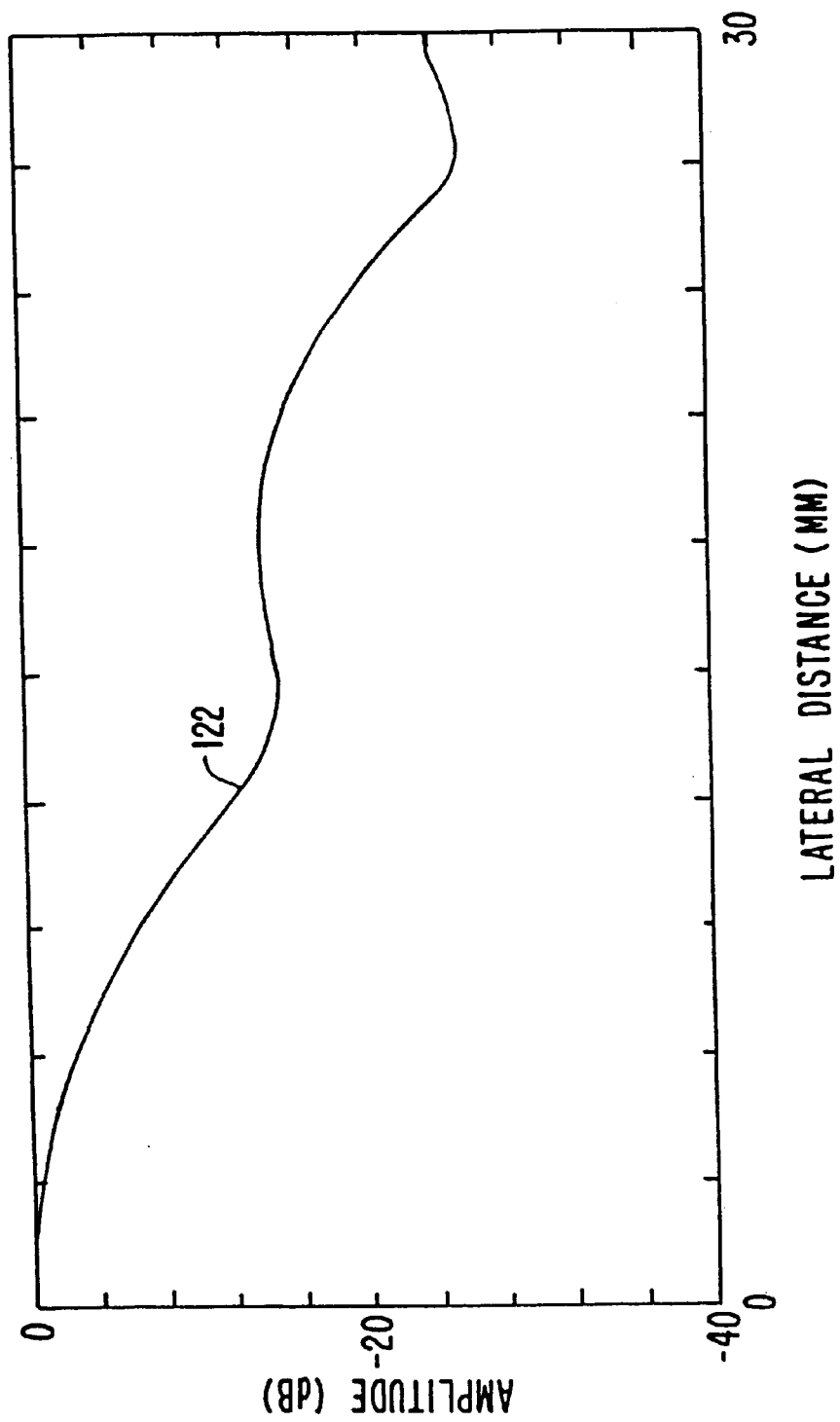
FIG. 12B illustrates another modeled lateral beam profile of the transducer of FIG. 11.

FIGS. 12A and 12B illustrate modeled lateral beam profiles 120 and 122 for the system of FIG. 11, featuring a 1 MHz unfocused transducer 25.4 mm in diameter. The beam profiles correspond to the ultrasound amplitudes perpendicular to axis A2 at depths of 107 mm and 200 mm from skin-contact window 117, which correspond to the center of focal region and the transducer far field.

Figure 13:
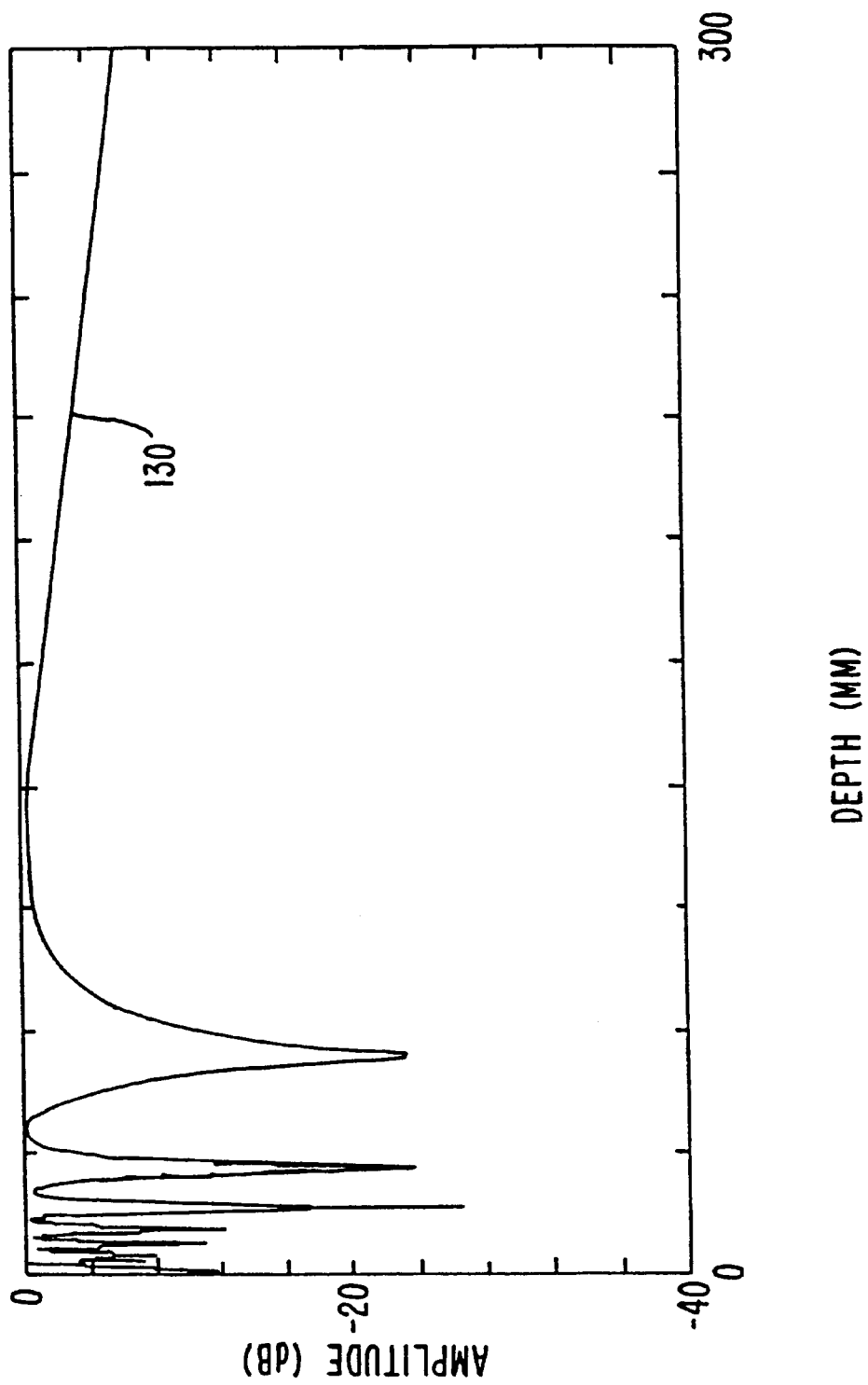
FIG. 13 illustrates a modeled axial beam profile of the transducer of FIG. 11.

FIG. 13 illustrates a modeled axial beam profile 130 for the same transducer. The beam profile corresponds to the ultrasound amplitude along central axis A2 of system 110 from the skin-contact window 117 (distance=0) to an axial distance of 100 mm from skin-contact window 117.

In this the most simple exemplary embodiment, the ultrasonic axial amplitude 130 is uniform to within 6 dB from approximately 62 mm off the transducer surface to approximately 300 mm off the surface. At the focal distance of 107 mm, the lateral profile 120 suggests uniformity to within 6 dB over a diameter of 10 mm. In the far field at 200 mm, the lateral profile 122 suggests uniformity to within 6 dB over a diameter of 17 mm. The length of transducer housing 111 and consequently the length of the water path 113 can be adjusted to position either the focal zone or any far field point onto the middle of the muscle injection point, such adjustment providing a corresponding ultrasonic beam width. It is seem that the lateral beam profiles 120 and 122 of FIGS. 12A and 12B offer substantially more uniform ultrasonic exposure than the near field profile 90 of FIG. 9.

Preferably, the present uniform wide field of ultrasound energy will vary by less than 10 dB (and more preferably 6 dB and most preferably 3 dB) across an axial distance from the skin contact window to a distance beyond the depth of the target region of interest.

Preferably as well, the present uniform wide field of ultrasound energy ill vary by less than 10 dB (and more preferably 6 dB and most preferably 3 dB) across beam width of at least 8 mm, more preferably 12 mm, and most preferably 35 mm.

Figure 14:
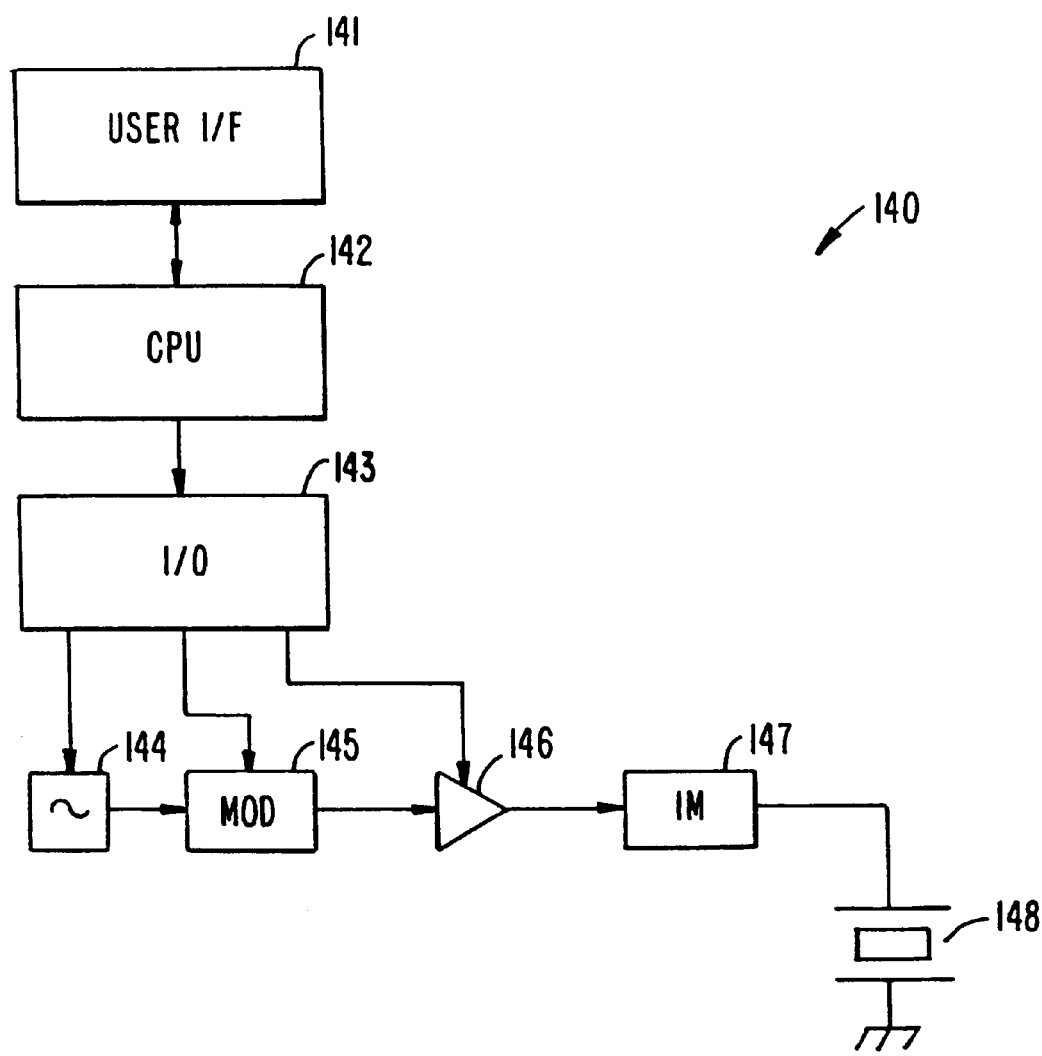
FIG. 14 depicts a simplified block diagram of an electronic system to drive the transducer of FIG. 11.

FIG. 14 depicts a simplified block diagram of an electronic system 140 to drive the transducer of FIG. 11. The user operates the system through a user interface 141 to a computer or controller subsystem 142. Through a digital I/O device 143, the computer controls a signal generator 144 to generate the RF driving signal, a modulator 145 to format the number of cycles per burst and to set the burst rate, a variable gain power amplifier 146, an impedance matching circuit 147, and finally the transducer 148.

In yet a further variation of the single element, wide beam device, the transducer may be coupled to the patient via a solid acoustic medium, or buffer rod, as compared to the fluid medium discussed above. The solid acoustic medium would thence be decoupled acoustically from the delivery device housing. Ideally, the solid medium would comprise a material with an acoustic impedance between that of the transducer piezoelectric ceramic (typically 33 Mrayls) and that of the patient (typically 1.5 Mrayls), and further would ideally have a minimum acoustic attenuation (ideally on the order of 0.1 dB/MHz/cm or less), as such attenuation would result in attenuation of the ultrasonic beam and consequent device heating. Candidate materials for the solid medium include aluminum metal and glass. For improved acoustic coupling to the patient, these solid medium materials might feature acoustic impedance matching layers, in the form of quarter wave length thickness of intermediate acoustic impedance materials generally from the families of polymers or loaded epoxies. Acoustic impedance matching methods are known to persons skilled in the art.

In the following paragraphs, further variations of wide beam ultrasound transducers of the present invention are presented. All of the construction and operational techniques from above apply equally to the following.

Figure 15:
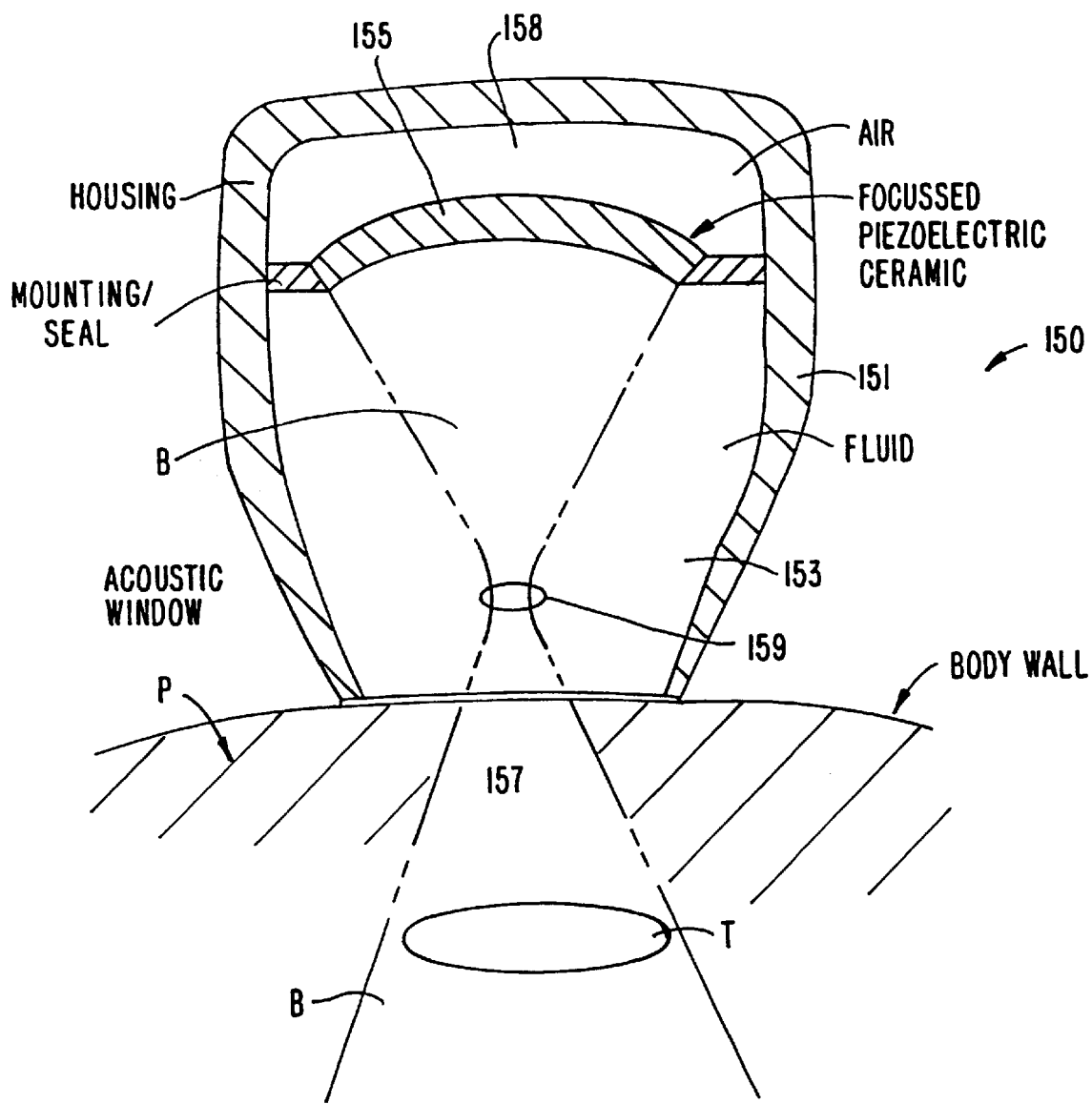
FIG. 15 is a sectional side elevation view of a second embodiment of the present wide aperture beam delivery system, having a curved ultrasound transducer.

FIG. 15 depicts an alternate embodiment 150 of the present wide aperture ultrasound beam delivery system in which a curved ultrasound transducer 155 is suspended within housing 151. Being curved, transducer 155 narrows the width of beam B of ultrasound energy which passes through fluid 153 and through skin-contact window 157, and which then broadens within the patient P. Similar to the above described system, an air pocket 158 is provided to ensure that maximal ultrasound energy emitted from transducer 155 passes towards and into patient P.

As seen in FIG. 15, beam B of ultrasound energy is narrowed through a focal region 159 which is disposed within fluid 153 such that a wide uniform field of ultrasound energy spreads across a rather large target region T in patient P into which DNA or other therapeutic biological substance has been injected. In this manner, the distance from the transducer 155 to target region T can be reduced for a smaller physical size of the delivery device.

Figure 16:
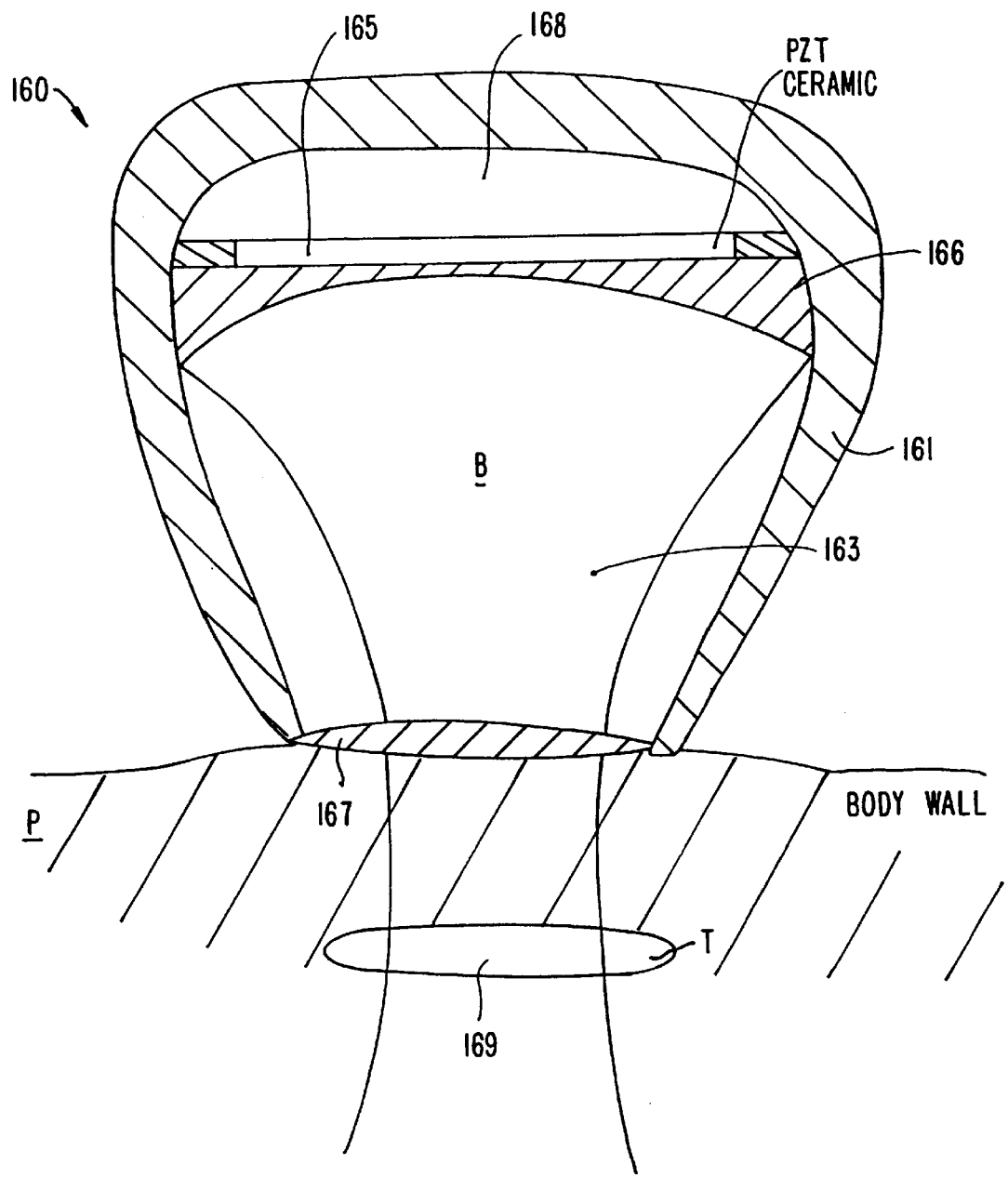
FIG. 16 is a sectional side elevation view of a third embodiment of the present wide aperture beam delivery system, having an acoustically-refractive material mounted to the transducer.

FIG. 16 shows yet another embodiment of the present invention in which an acoustically refractive material 166 is mounted to ultrasound transducer 165 to shape the acoustic beam B to a focal region 169 at an appropriate depth in patient P. In a preferred aspect, acoustically refractive material 166 may comprise silicon rubber (convex lens) in which the velocity of sound is about 1.0 mm/μsec, or epoxies or plastics (concave lens) with sound velocities of about 2.5 mm/μsec, as compared to water which has a velocity of sound passing there through of about 1.5 mm/μsec. Keeping the acoustic impedances of the refractive materials close to that of water will reduce the amount of internal reflection and standing waves in the device. Additionally, skin-contact window 167 may have a curved shape to assist in further narrowing or widening beam B of ultrasound energy passing therethrough.

Figure 17:
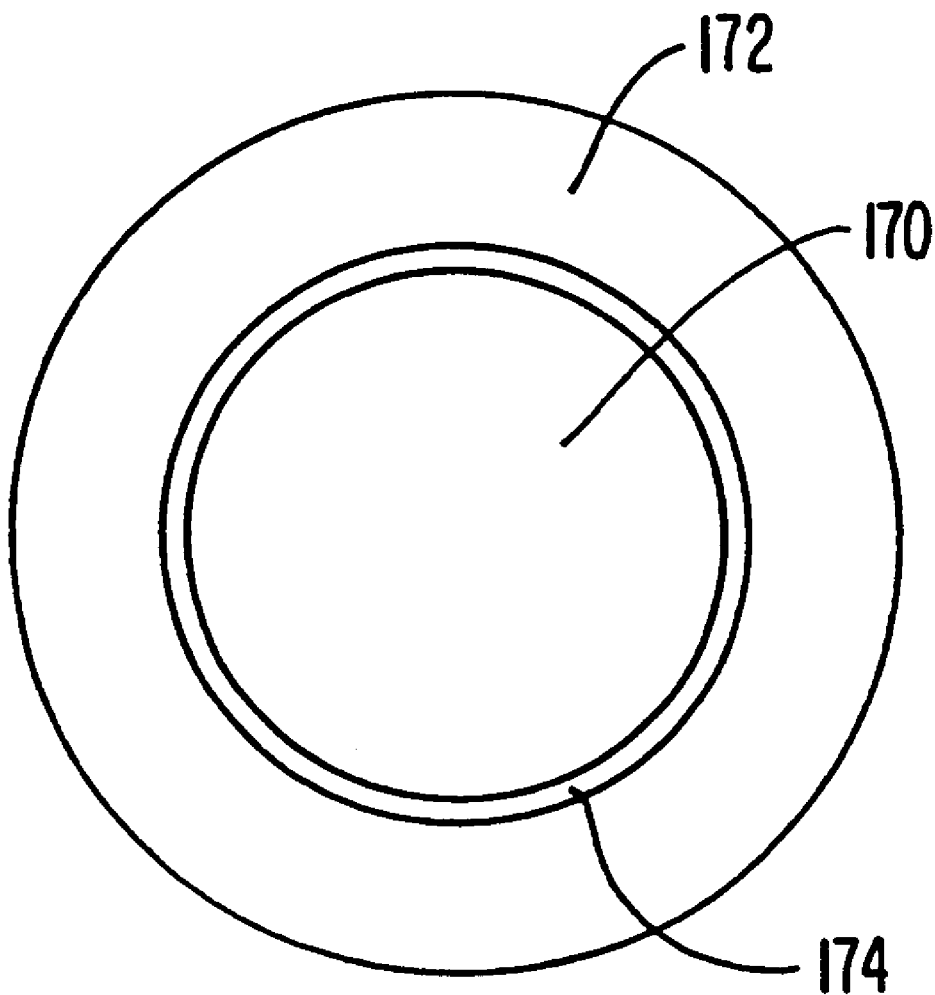
FIG. 17 is a front view of the acoustic aperture of an annular array transducer.

The single element beam profiles depicted in FIGS. 12A and 12B can be substantially broadened by the addition of an annulus 172 around a central disc 170, as depicted in FIG. 17. In an exemplary embodiment, the outer diameter of the annulus is equal to the square root of two times the outer diameter of the central disc. The gap between the central disc and the annulus shall be sufficient to prevent acoustic cross talk between the two pieces of piezoelectric ceramic.

Figure 18:
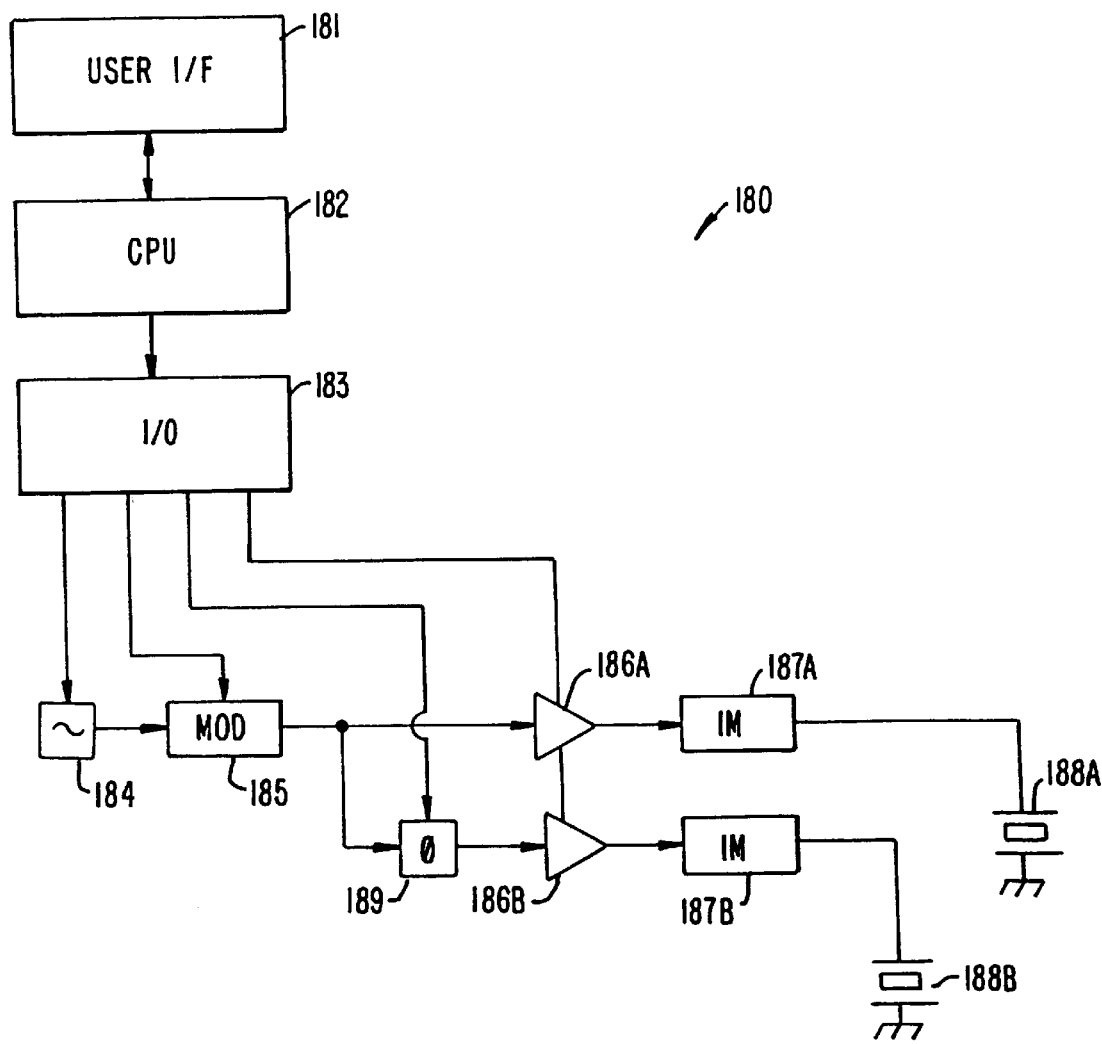
FIG. 18 depicts a simplified block diagram of an electronic system to drive the transducer of FIG. 17.

FIG. 18 depicts a simplified block diagram of an electronic system 180 to drive the transducer of FIG. 17. The user operates the system through a user interface 181 to a computer or controller subsystem 182. Through a digital I/O device 183, the computer controls a signal generator 184 to generate the RF driving signal, a modulator 185 to format the number of cycles per burst and to set the burst rate, a time delay or phase shifting circuit 189, variable gain power amplifiers 186A and 186B, impedance matching circuits 187A and 187B, and finally the transducers 188A and 188B. The amplifiers 186A and 186B need not be operated at the same gain setting. Furthermore, the phase shifting circuit can be set for any angle from zero to 360 degrees.

Figure 19:
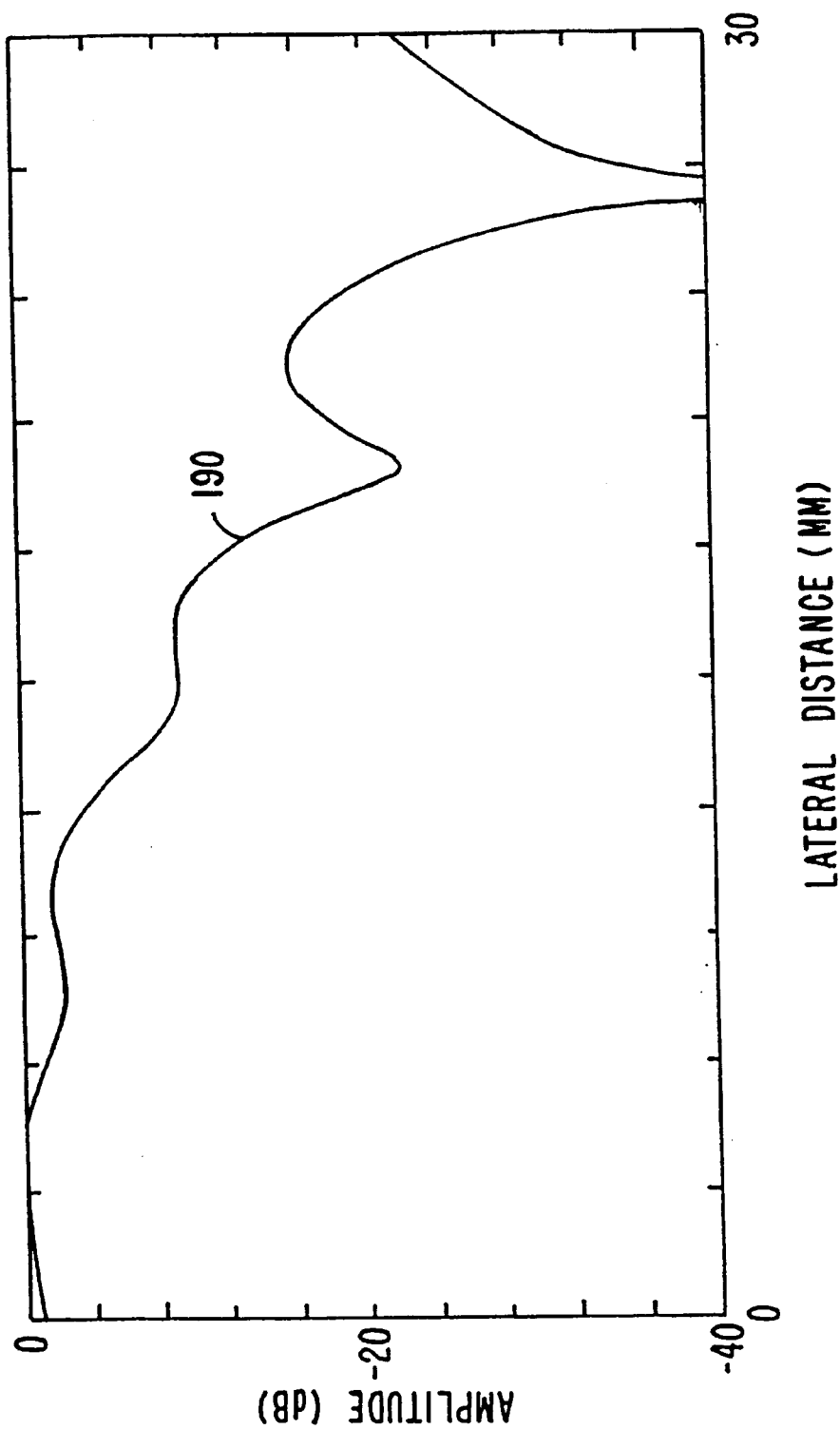
FIG. 19 illustrates a modeled lateral beam profile of the transducer of FIG. 17.

In an exemplary application, the phase shifter was set to zero and amplifiers 186B and 186B had gain settings in the ratio 1.0:0.5. FIG. 19 depicts a modeled lateral beam profile 190. Of particular note, the 6 dB beam width has now been opened up to 25.5 mm, albeit at an approximately 10 dB loss of signal strength.

Figure 20:
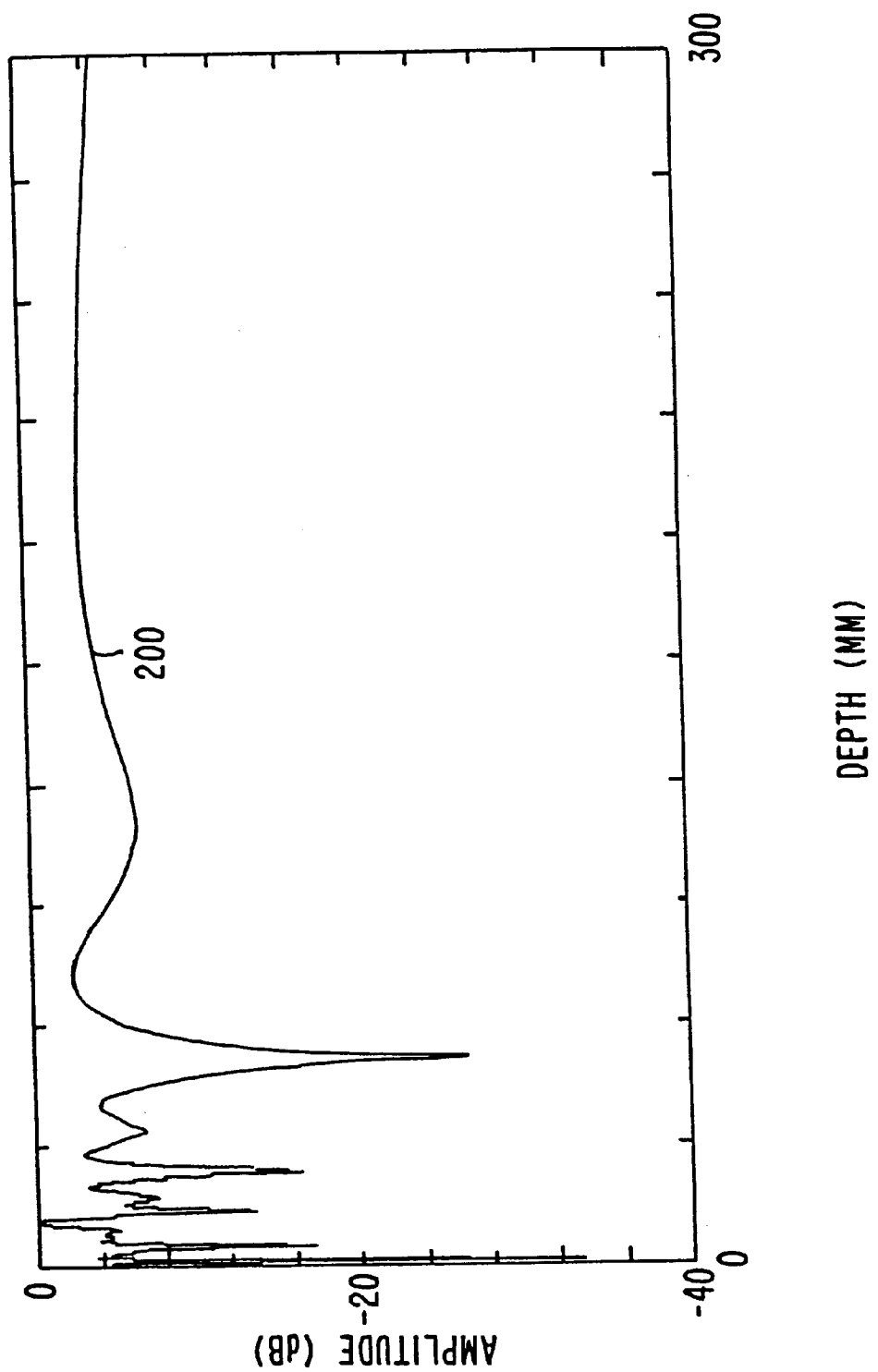
FIG. 20 illustrates the modeled axial beam profile of the transducer of FIG. 17.
Figure 21A:
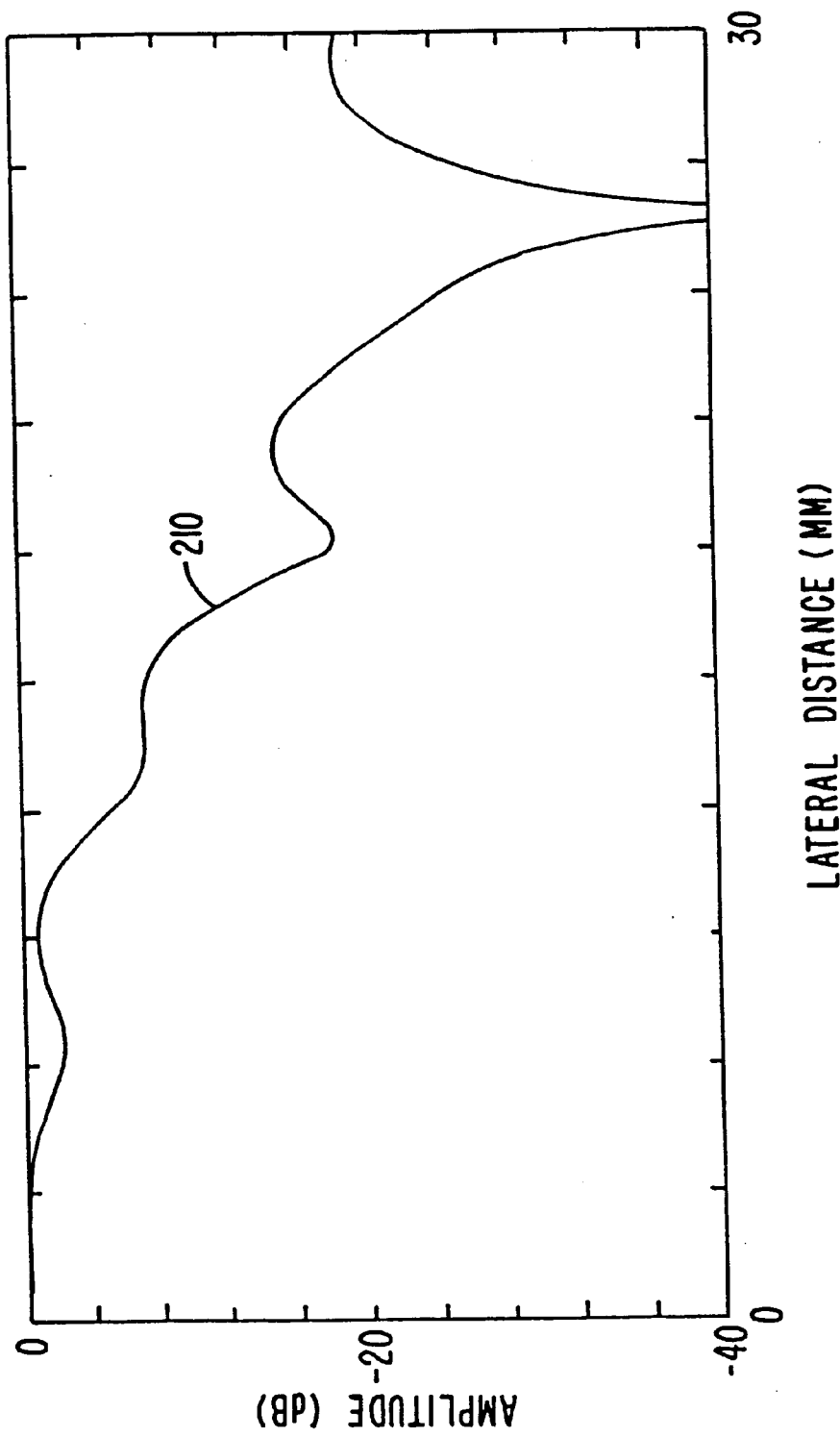
FIG. 21A illustrates a modeled proximal lateral beam profile of the transducer of FIG. 17.
Figure 21B:
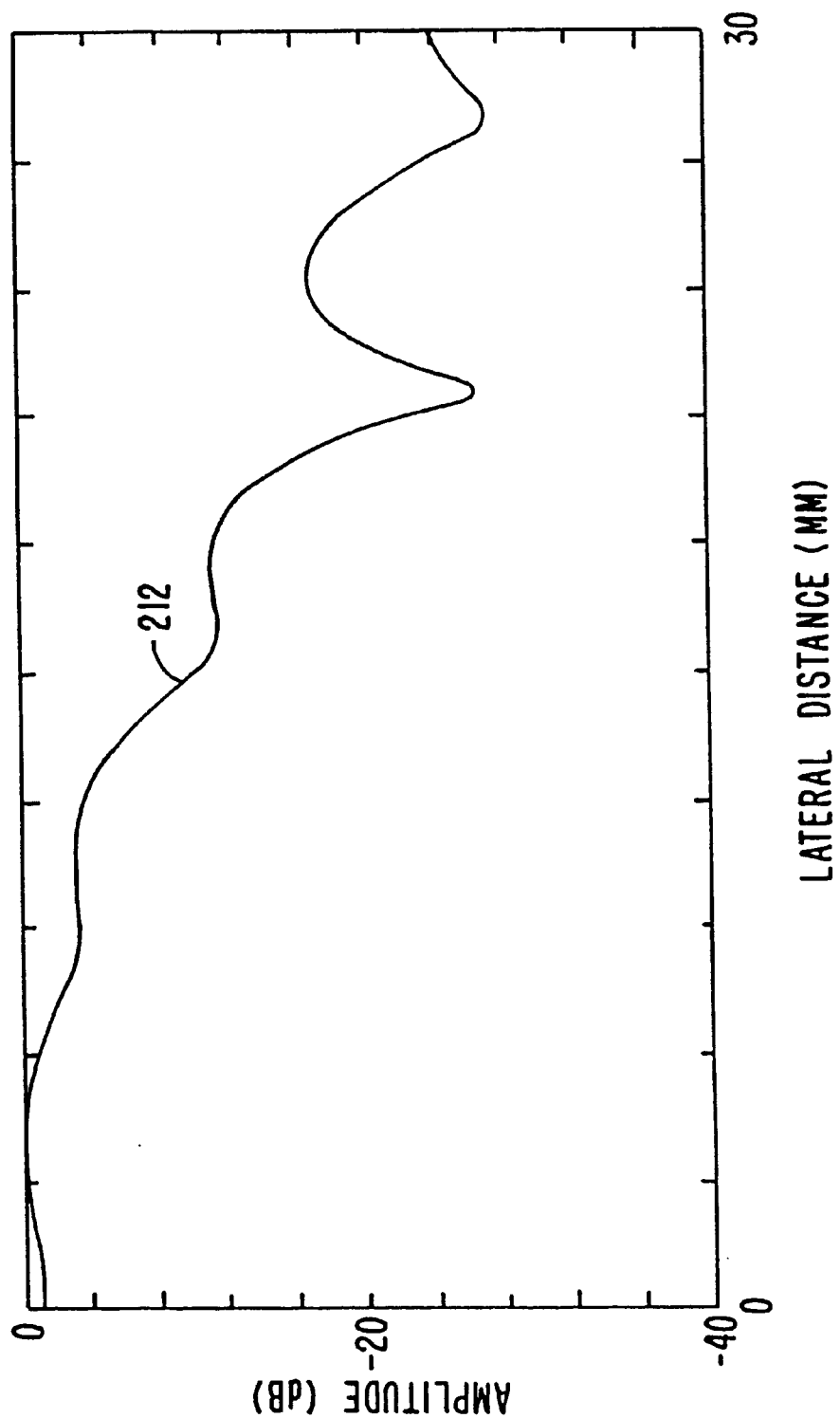
FIG. 21B illustrates a distal lateral beam profile of the transducer of FIG. 17.

Beam broadening comes about by the depression of the main lobe of the ultrasonic beam and enhancement of the side lobes. FIG. 20 depicts the modeled axial profile 200 for this central disc and annulus pair, showing the 10 dB depression in the focal zone, when compared with the modeled axial profile of FIG. 13. FIGS. 21A and 21B depict modeled lateral beam profiles at 10 mm proximal and 10 mm distal with respect to the lateral profile of FIG. 19, showing retention of a wide beam over depths of field relevant to the current applications. Specifically, FIGS. 21A and 21B show profiles with 6 dB beam widths of 24.3 mm and 26.8 mm, respectively.

It is to be understood that the present invention is not limited to one annulus around a central disc, with the specific amplitudes and phases of the driving signals as stated above. Indeed, in the extreme, an infinite set of annuli with an infinite aperture can be programmed to generate a perfectly square beam profile with no ripple across the beam. With regard to driving electronics, additional channels comprising a phase shifter or time delay, power amplifier, and impedance matching circuit will be required.

Figure 22:
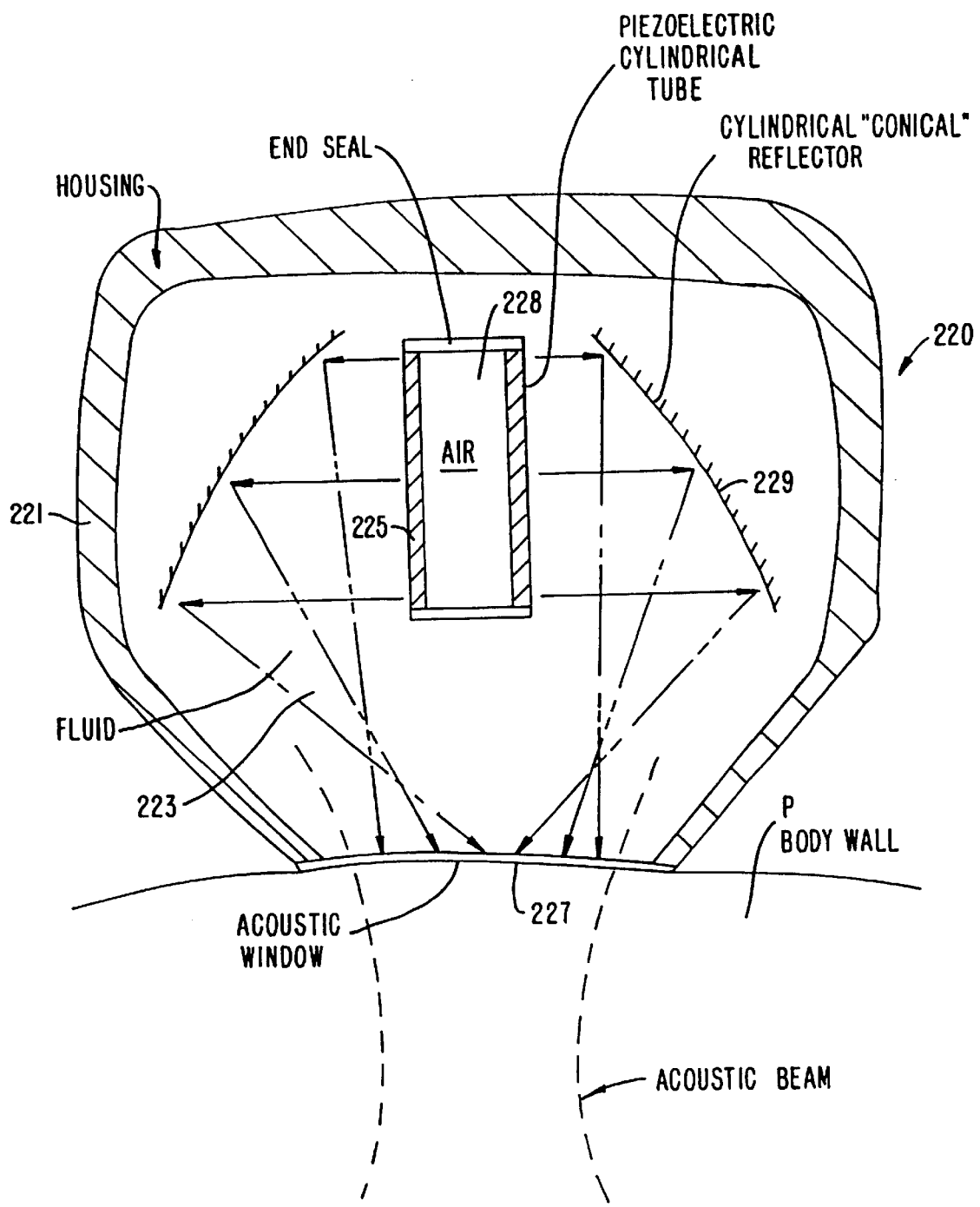
FIG. 22 is a sectional side elevation view of a fourth embodiment of the present wide aperture beam delivery system, having a cylindrical-shaped transducer.

FIG. 22 shows yet another embodiment of the present invention in which a cylindrical-shaped ultrasound transducer 225 is suspended within housing 221. In this aspect of the invention, transducer 225 preferably has a hollow, air-filled interior 228 such that ultrasound energy emitted by transducer 225 is directed radially outwards through fluid 223 towards curved acoustic reflector 229, which in turn reflects and directs the beam of ultrasound energy passing through skin-contact window 227, and into patient P. An advantage of this invention is that it provides a compact housing for shaping a therapeutic ultrasound beam at a preferred depth within a patient. This design also provides a greater surface area of the piezoelectric ceramic for greater ultrasonic energy delivery.

Figure 23:
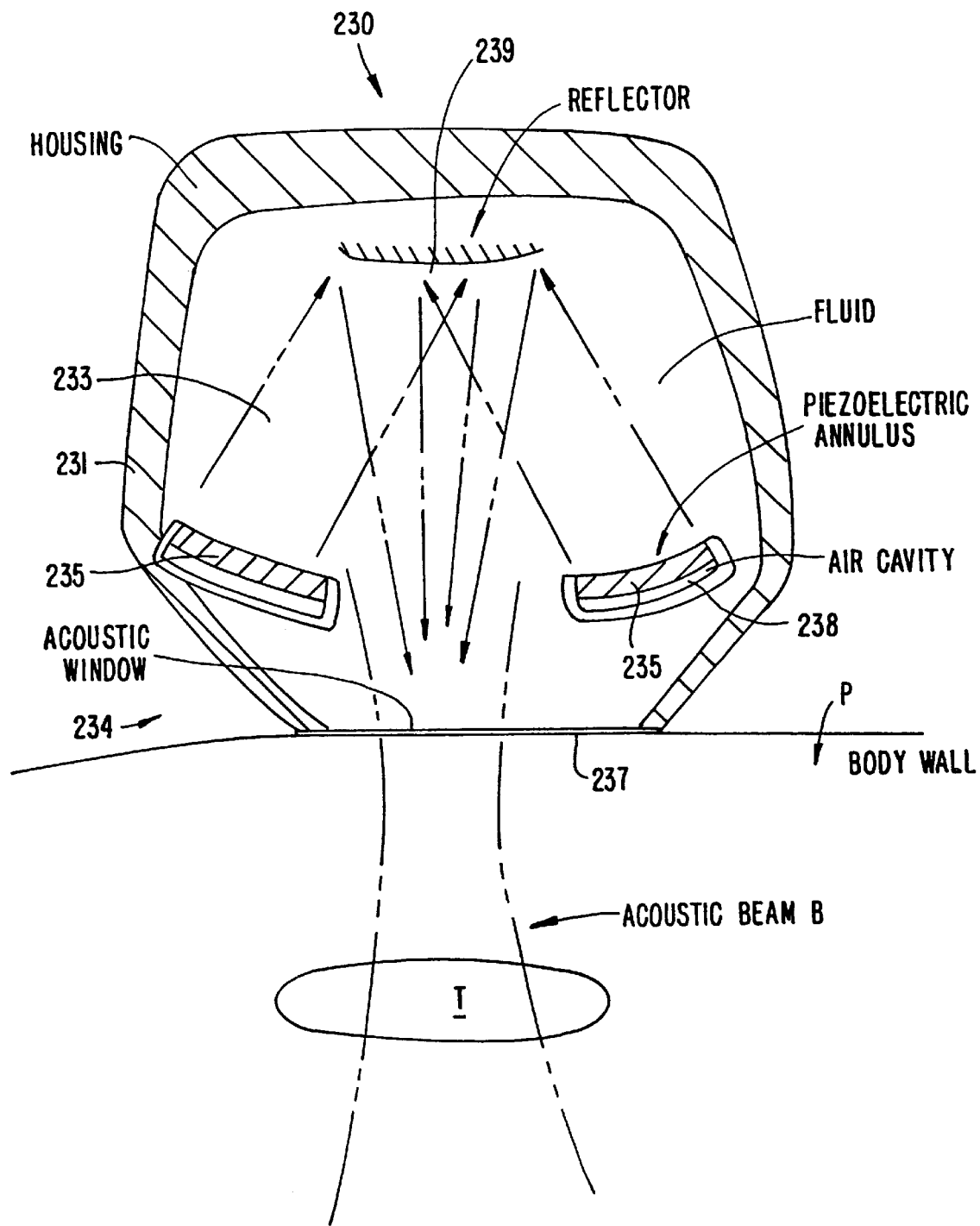
FIG. 23 is a sectional side elevation view of a fifth embodiment of the present wide aperture beam delivery system, having an annular-shaped transducer.

FIG. 23 shows yet another embodiment of the present invention in which an annular-shaped ultrasound transducer 235 is disposed near distal end 234 of housing 231. Transducer 235 directs ultrasound energy through fluid 233 towards acoustic reflector 239, which in turn directs the ultrasound energy through fluid 233 and through skin-contact window 237, passing into patient P. In this embodiment, both transducer 235 and acoustic reflector 239 can be curved, either convexly or concavely, to assist in focussing or defocusing the beam of ultrasound energy to a target region T in the patient. An advantage of this embodiment of the invention is that a large ratio of transducer cross sectional area to beam cross sectional area can be achieved, offering a greater margin on the drive capabilities, thus allowing the piezoelectric ceramic to be driven at comparatively lower voltages. An annular air pocket 238 is provided behind transducer 235 such that substantially all of the ultrasound energy emitted from transducer 235 is directed towards acoustic reflector 239.

Figure 24:
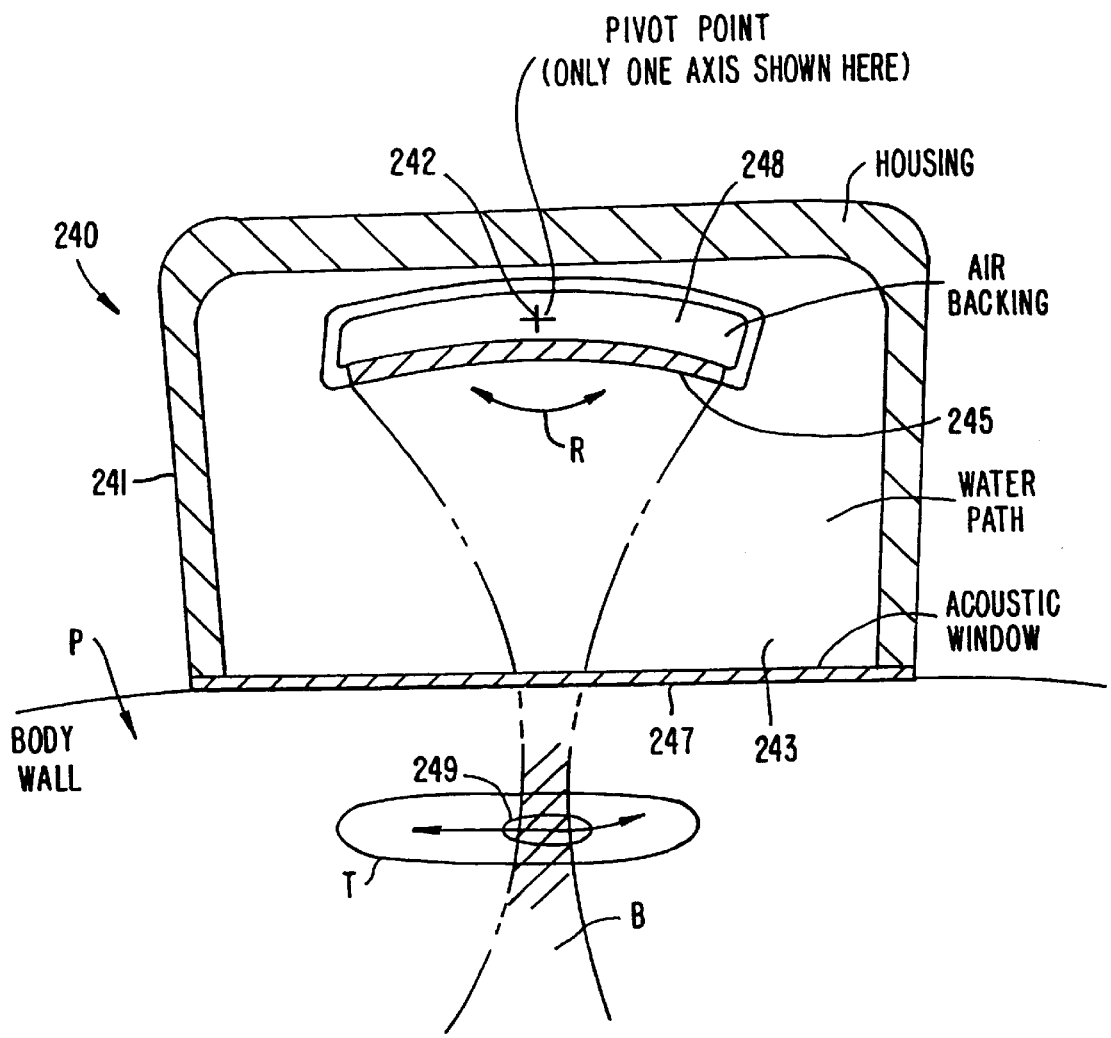
FIG. 24 is a sectional side elevation view of a sixth embodiment of the present wide aperture beam delivery system, adapted to raster scan a therapeutic ultrasound beam.

In the event that the region of interest in the patient's body is greater than what might be easily covered by the placement of a single transducer, or what might be covered by sequential stepping of transducer placement, scanning techniques may be employed. As depicted in FIG. 24, delivery device 240 comprises a housing 241 in which ultrasound transducer 245 is mounted on preferentially orthogonal axes to rotate back and forth about pivot points 242 (only one pivot point shown for ease of illustration). As such, transducer 245 is adapted to rotate about pivot point 242 in two perpendicular axes such that a narrowed beam 249 of therapeutic ultrasound energy can be raster-scanned across target region T.

Figure 25:
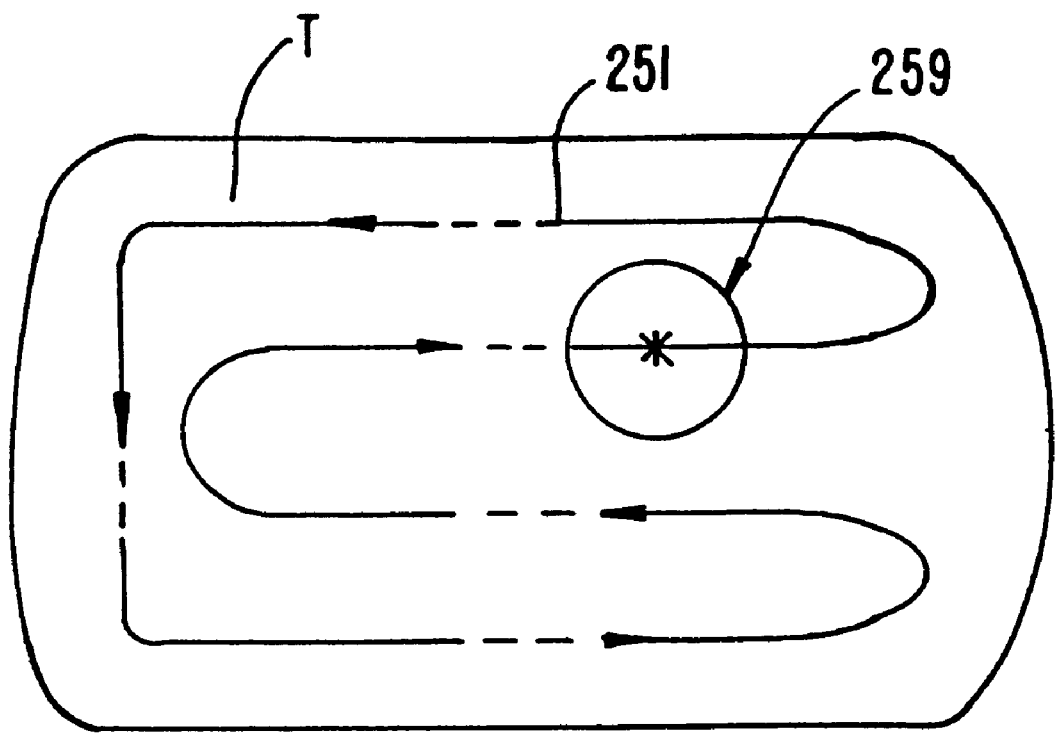
FIG. 25 is a top plan view of the raster scan generated by the system of FIG. 24.

A typical top plan view of a raster scan 251 generated by the system of FIG. 24 is shown in FIG. 25 in which a narrow diameter focal region 259 is raster scanned across a larger diameter target region T. If it is desired to achieve a specific duty cycle of ultrasonic emission at any point in the target region, the physical distance of continuous emission of the raster scan transducer may be adjusted. A specific percentage duty cycle requires that the effective beam width of the transducer be over the specific point in the sample for the same percentage of time (continuous or a higher burst rate emission from the transducer is now required).

Any of the transducers as depicted in FIGS. 11, 15, 16, 17, 22, and 23 may be mounted in the pivot points 242 of the delivery device 240 of FIG. 24. All of the individual features may be collected in whole or in part in the assembly of the delivery device.

Figure 26:
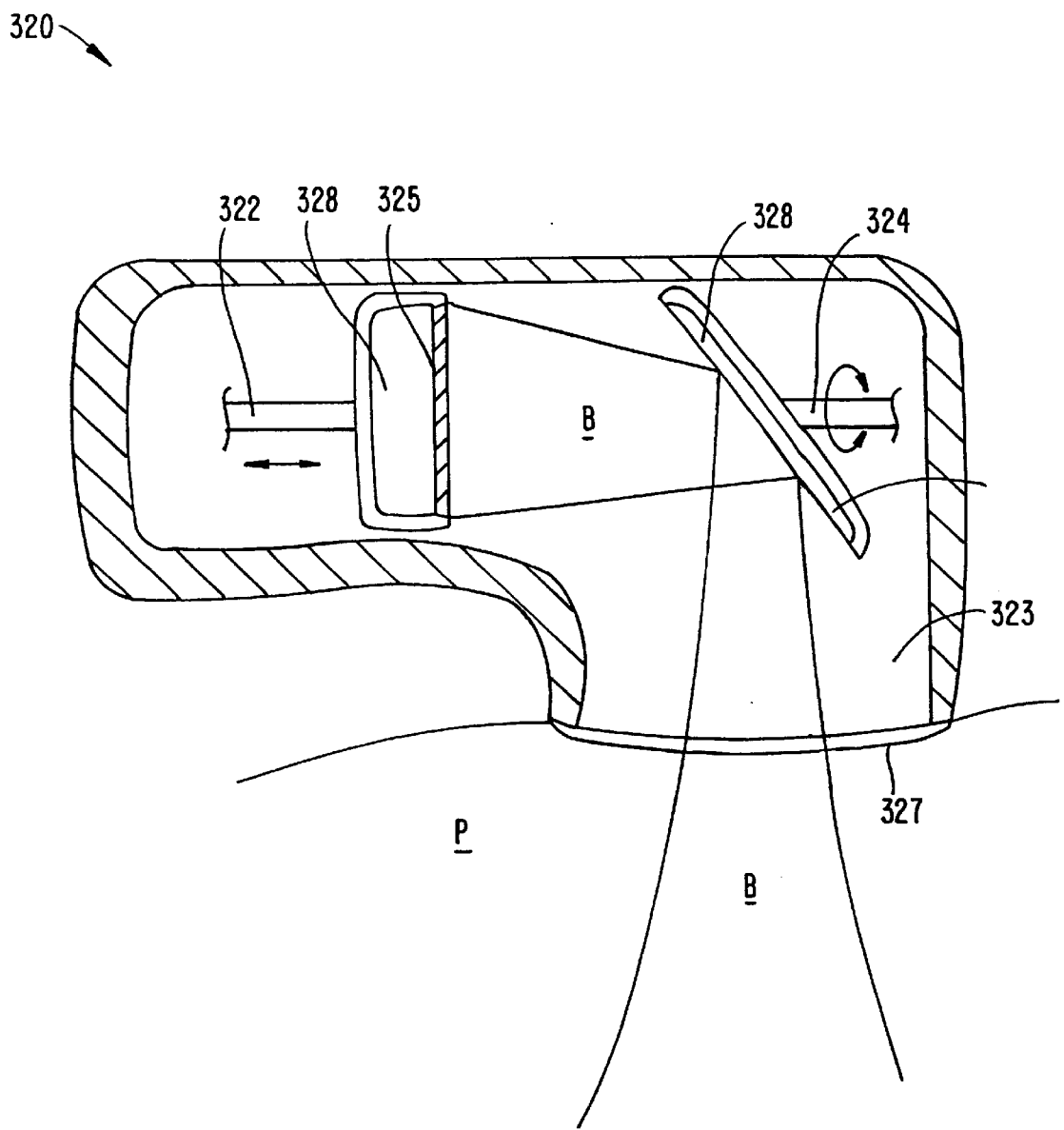
FIG. 26 is a sectional side elevation view of a sixth embodiment of the present wide aperture beam delivery system, comprising a depth adjusted transducer and a rotating ultrasonic mirror.

FIG. 26 depicts yet another scanning ultrasound delivery device 320 in which the transducer 325 with its air backing cavity is mounted with the ultrasonic beam B parallel to the surface of the patient. The ultrasonic beam B passed though the fluid medium 323, reflects of an acoustic mirror 321 with air backing 328, and proceeds though patient coupling window 327 into the patient P. The provision of an air backing behind the mirror eliminates any possibility of refractive ultrasonic energy entering the mirror and reradiating in destructive interference with the primary ultrasonic beam. The reflective surface may be planar or curved for narrowing or widening the ultrasonic beam B. By mounting the transducer on longitudinal shaft 322, the transducer may be pushed forward or pulled backward so as to cause the focal point or the point of optimal ultrasonic beam to be placed deeper of shallower in the patient. By mounting the mirror rotational shaft 324, the mirror can be rotated or toggled, thus sweeping the ultrasonic beam B across a section of the patient.

Figure 27:
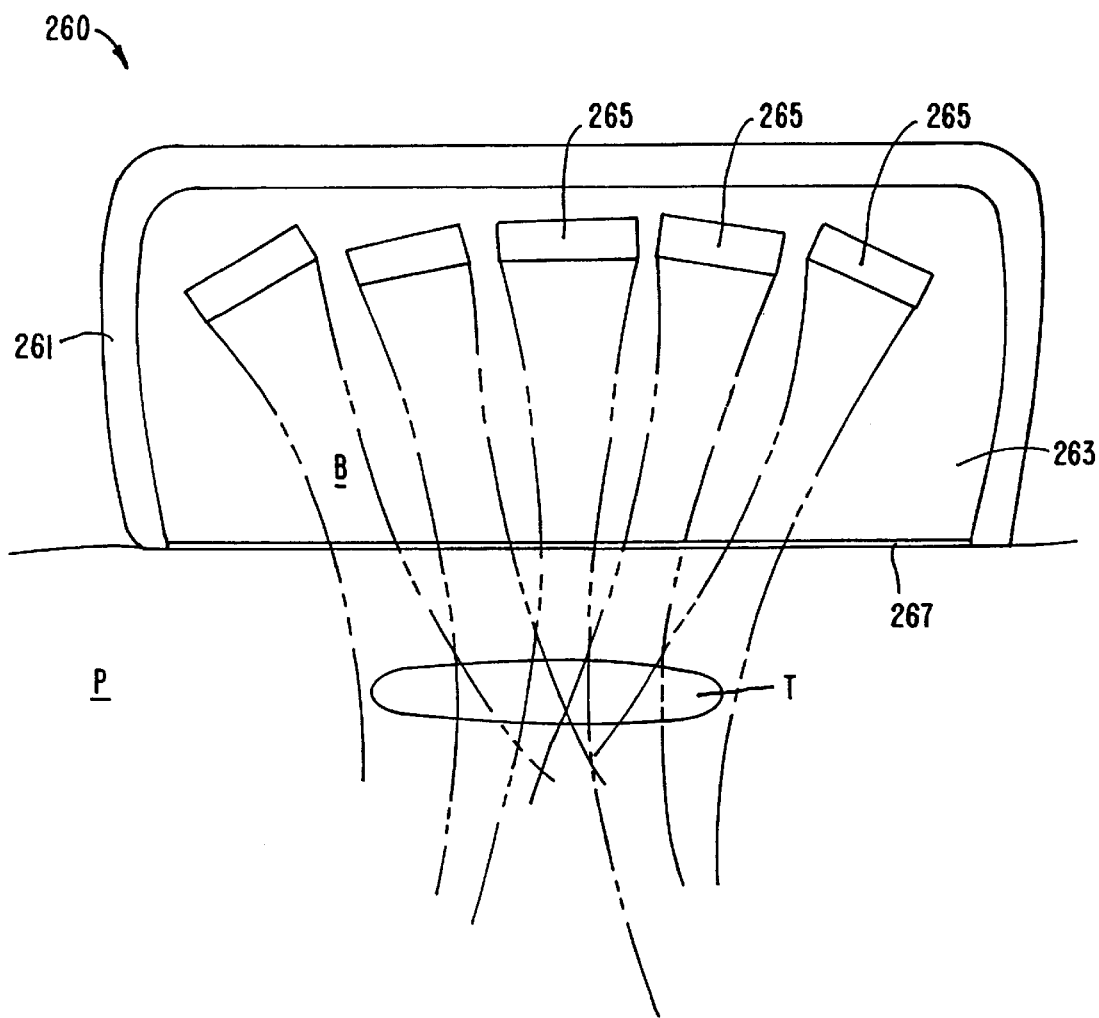
FIG. 27 is a sectional side elevation view of a seventh embodiment of the present wide aperture beam delivery system, comprising a plurality of individual transducers.

FIG. 27 depicts yet a further scanning ultrasound delivery device 260, comprising a multitude of single element or annular array transducers 265 of the type as described above, with or without narrowing or widening means, for the purpose of illuminating a yet larger area. The transducers might be mounted in a single file or may be arranged in parallel rows (not shown for ease of illustration). The delivery device housing 261 will contain fluid 263 for the propagation of ultrasonic energy from transducers 265 to the device housing window 267 and into the patient P. If the transducers 265 are larger in lateral dimensions than their acoustic beams in the target region T of the patient, then the transducers can be mounted in a tilted manner as shown.

Figure 28:
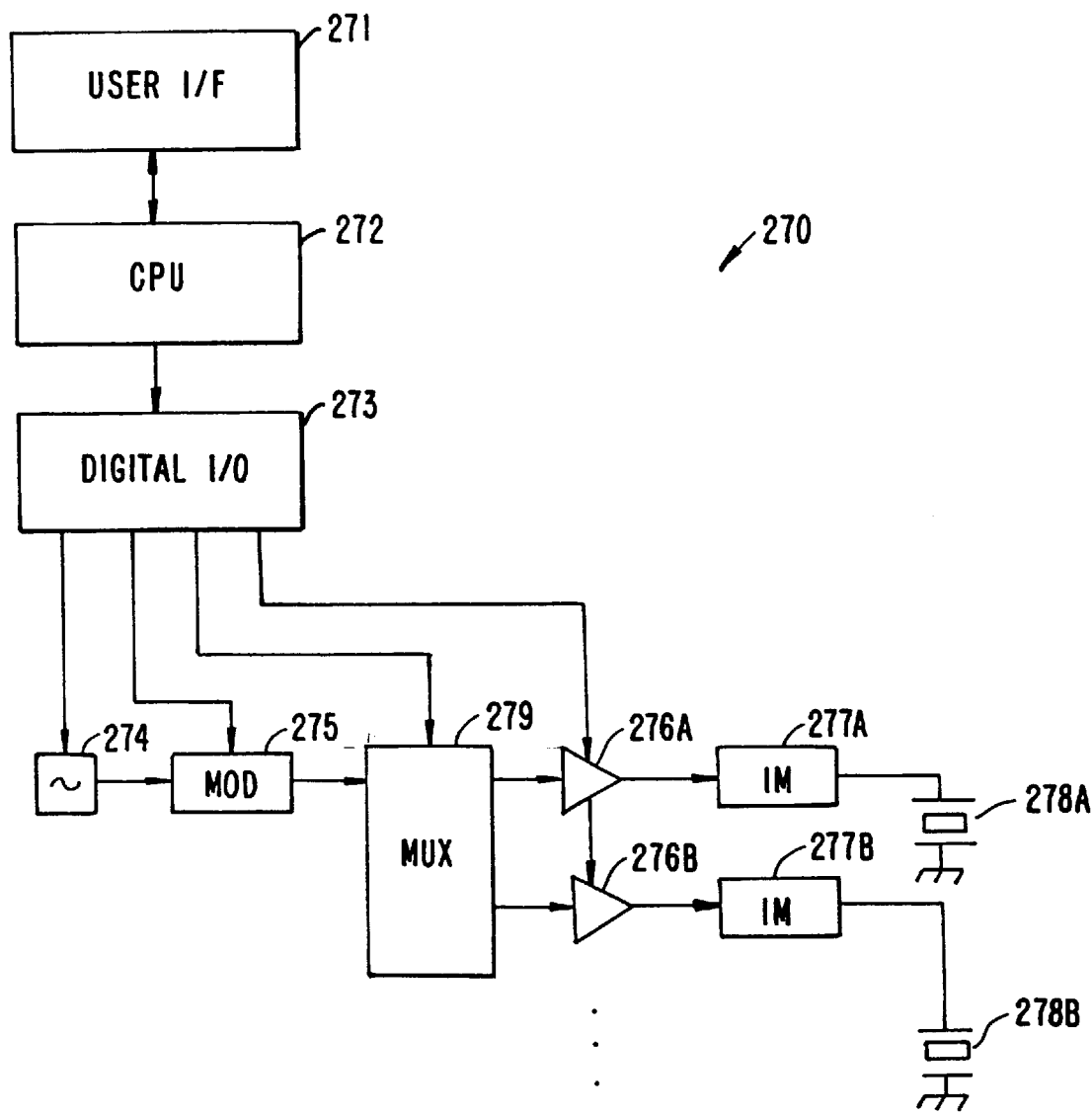
FIG. 28 depicts a simplified block diagram of an electronic system to drive he transducer of FIG. 27.

Several methods exist for driving the array of transducers in delivery device 260. In an exemplary technique, the signal generator system 270 as sketched in FIG. 28 comprises a central controller 272 with drives a frequency generator 274, a modulator 275, a switch (multiplexer) 279, and amplifiers 276 and impedance matching circuits 277 for each transducer 278 in the array. The controller sequentially switches the signal from the output of the modulator or preamplifier stage to the final amplifier stage of the respective transducer channels, thus driving all transducers sequentially during one pulse repetition period. This makes the assumption that the product of the duty cycle and the number of devices is less than one. If this assumption is not warranted, then one or more individual transducers might be assigned to a single channel, provided that the transmitted ultrasonic beams do not overlap. In this manner higher duty cycles can be achieved on each transducer.

In accordance with the present invention, therefore, individual transducers 265 may be operated such that their activation is staggered, with each transducer, or combinations of transducers, being turned on and off in sequence. An advantage of separately controlling the operation of each of transducers 265 individually is that system duty cycle can be increased. Moreover, when operating a plurality of transducers at the same time, it may be preferable to operate transducers which are spaced apart from one another, so as to avoid constructive or destructive interference between their respective ultrasound beams.

Figure 29:
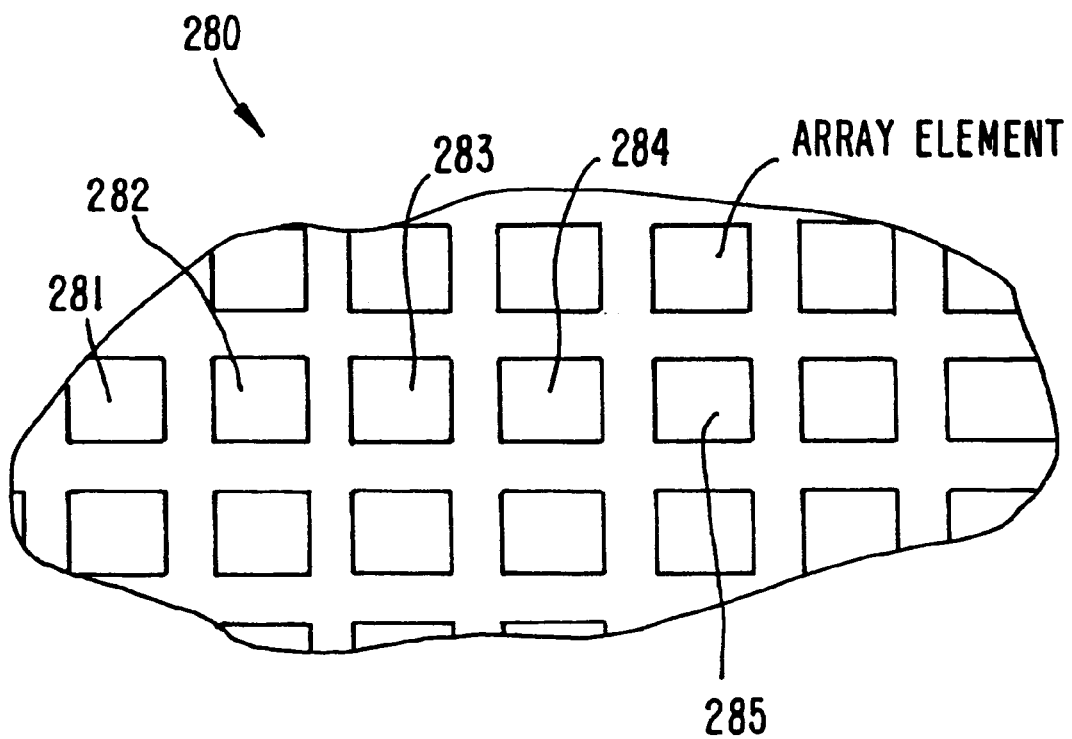
FIG. 29 is a front view of a eighth embodiment of the present wide aperture beam delivery system, comprising a two dimensional transducer array.
Figure 30:
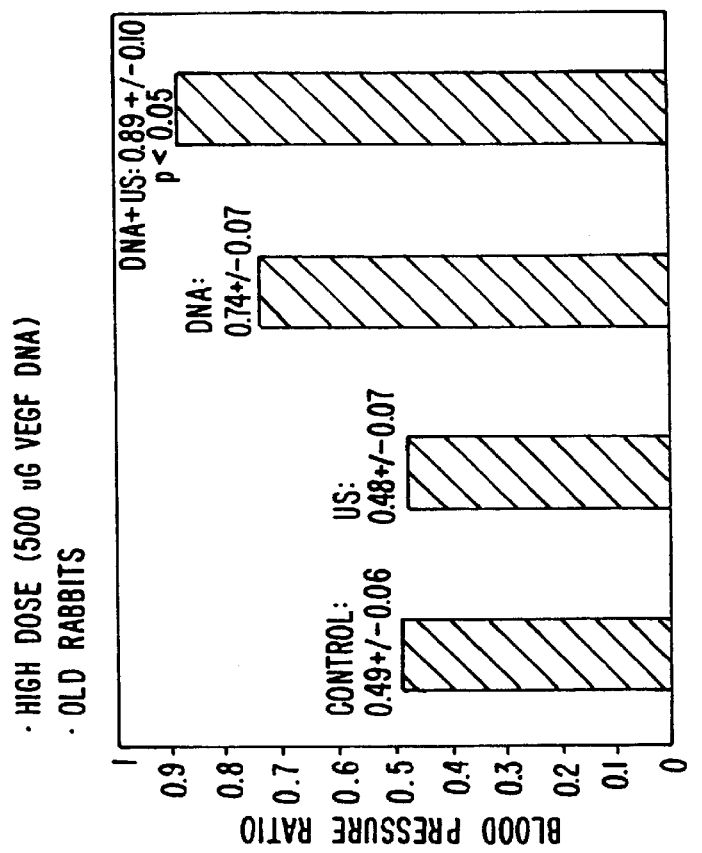
FIG. 30 graphically presents blood pressure ratio data for rabbit ischemic hind limb experiments.
Figure 30:
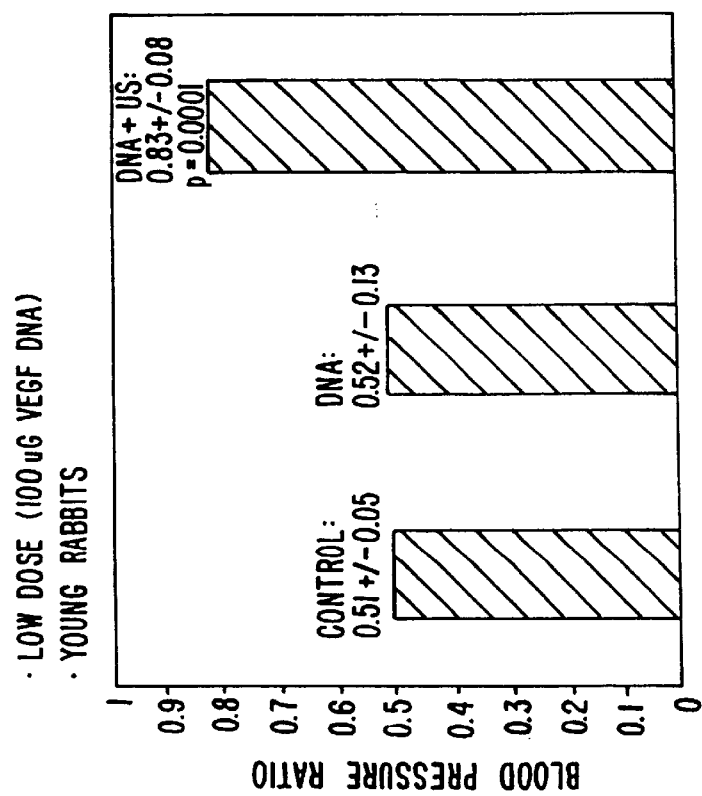

FIG. 29 shows a two dimensional ultrasound transducer array 280, comprising a plurality of individual ultrasound transducer elements 281, 282, 283, etc. In preferred aspects, each of ultrasound elements 281, 282, 283, etc. are preferably individually controlled with a dedicated time delay and power amplifier such that the phases of the signals of each of elements 281, 282, 283, etc., could be adjusted to direct a shaped composite ultrasound beam to a specific location within the patient's body, or alternatively, to sweep the beam with a specified beam width in a raster scan. Each of the elements 281, 282, 283, etc. must be of sufficiently small size such that their beam widths cover the total region of interest.

The transducer array of FIG. 29 may be mounted within a fluid filled housing as described herein, or may alternatively be applied directly to the patient's skin.

EXPERIMENTAL

Experiment Number One

As is described in copending U.S. patent application Ser. No. 09/364,616, prototype hardware as depicted in FIG. 11, specifically comprising an ultrasound delivery system having a 25.4 mm diameter 1 MHz unfocussed transducer with a 10 cm water path distance and with a 25.4 mm diameter skin contact window, was used to sonicate the thigh muscles of New Zealand white rabbits following injection of beta-galactosidase plasmid DNA into the same. Plasmid DNA was injected into one site on the thigh muscle, followed immediately by ultrasound exposure at five sites on and in close proximity to the injection site. Each ultrasound exposure featured a beam width of approximately 10 mm, for 60 seconds, at an MI level of approximately 1.8, with a duty cycle of six percent (30 cycles at 1890 Hz repetition rate) and for a calculated increase in tissue temperature of less than 5 degrees Centigrade.

After five days the animals were sacrificed. Each thigh had 9 samples collected in a 3 by 3 array in the area exposed to ultrasound. The muscle samples had dimensions of about 1×1×0.5 cm(W×L×H). Protein was then extracted from the tissue and measured for beta-galactosidase enzyme activity and total protein. Beta-galactosidase activity was normalized to the protein content and expressed as activity per protein mass. For each rabbit thigh, an average beta-galactosidase activity was then calculated from the 9 samples.

The results are summarized in Tables 1 and 2 where no ultrasound (No US) and three ultrasound (US) conditions are compared. Expression levels are presented for each treatment comprising the mean beta-galactosidase activity from 9 to 11 rabbits for each group. The ultrasound condition, 1 MHz, 1.8 MI (mechanical index), 6% duty cycle, yielded the best results showing about a 25 fold enhancement of transfection versus the No US exposure conditions and other ultrasound conditions as set forth below.

TABLE 1

INTRAMUSCULAR GENE DELIVERY: RESULTS

| Treatment | N | B-gal/mg | Bkgrnd Correction | US/no US |
|---|---|---|---|---|
| No US | 10 | 49.8 +/− 30. | 5.5 | — |
| 1 MHz, 2 MI, 1.5% DC | 11 | 102.3 +/− 103* | 58.0 | 10.5 |
| 1 MHz, 0.5 MI, 25% DC | 9 | 124.0 +/− 81.2** | 79.7 | 14.5 |
| 1 MHz, 1.8 MI, 6% DC | 9 | 179.1 +/− 77.7** | 134.8 | 24.5 |

Background: 44.3
*p = 0.0153
**p = 0.0001

In low frequency exposures, conducted at 193 kHz with similar transfection conditions, the effect of the ultrasound was studied and results are presented in Table 2. With 193 KHz, 1.09 MI, 1.3% duty cycle about a nine fold increase in beta-galactosidase expression was observed compared to the No US condition.

TABLE 2

INTRAMUSCULAR GENE DELIVERY: RESULTS

| Treatment | N | B-gal/mg | Bkgrnd Correction | US/no US |
|---|---|---|---|---|
| No US | 3 | 114.2 +/− 123.9 | 47.6 | — |
| 194 kHz, 1.09 Mi, 1.3% DC | 3 | 526.0 +/− 43.2 | 459.4 | 9.7 |

Background: 66.6

In a second part of this experiment, an ultrasound pretreatment was applied. Specifically, the above experiment was repeated as set out above with the 5 US exposures carried out for the one injection site at 1 MHz, 1.8 MI, 6% DC conditions, however, the US was applied prior to the beta-galactosidase plasmid DNA injection. The US pretreatment achieved a 10.5 fold (58/5.5) increase in beta-galactosidase transfection, as compared to the 24.5 fold (135/5.5) increase in beta-galactosidase transfection achieved by applying the US after the beta-galactosidase injection, as illustrated in Table 1 above.

Experiment Number Two

As is described in copending U.S. patent application Ser. No. 09/364,616, ischemia was created in the rabbit hind limb by the complete removal of the internal femoral artery ten days before treatment. The rabbits were evaluated 30 days post treatment in three areas: blood pressure ratio—the ratio of blood pressure in the ankle of the ischemic hind limb compared to that in untouched animals; blood flow—the flow rate measured at the distal end of the iliac artery with a Doppler flow wire; and angiographic score—the number of native arteries, collateral arteries, and capillaries visible in each square of a grid on an angiographic image. In a first experiment, 100 micro grams of VEGF expressing plasmid DNA was injected into the hind limbs of young rabbits. In a second experiment, 500 micro grams of VEGF expressing plasmid DNA was injected into the hind limbs of old rabbits. Old rabbits were specifically selected for the second experiment because they are angiogenetically impaired. The use of a higher dose of VEGF expressing plasmid DNA in these animals would allow the demonstration of an ultrasonic enhancement in a normally plateaued, or saturated, biological system.

In both the first and second parts of the experiment, VEGF expressing plasmid DNA was injected into five sites on the thigh muscle followed immediately by ultrasound exposure of seven sites in close proximity to the injection sites. Ultrasound in the range of 1 MHz, 1.8 MI and 6% duty cycle was applied with the wide beam delivery system illustrated in FIG. 11. Comparisons were made to a rabbit control group and between rabbit groups to which ultrasound was, and was not, applied immediately following the VEGF expressing DNA injection.

Figure 31:
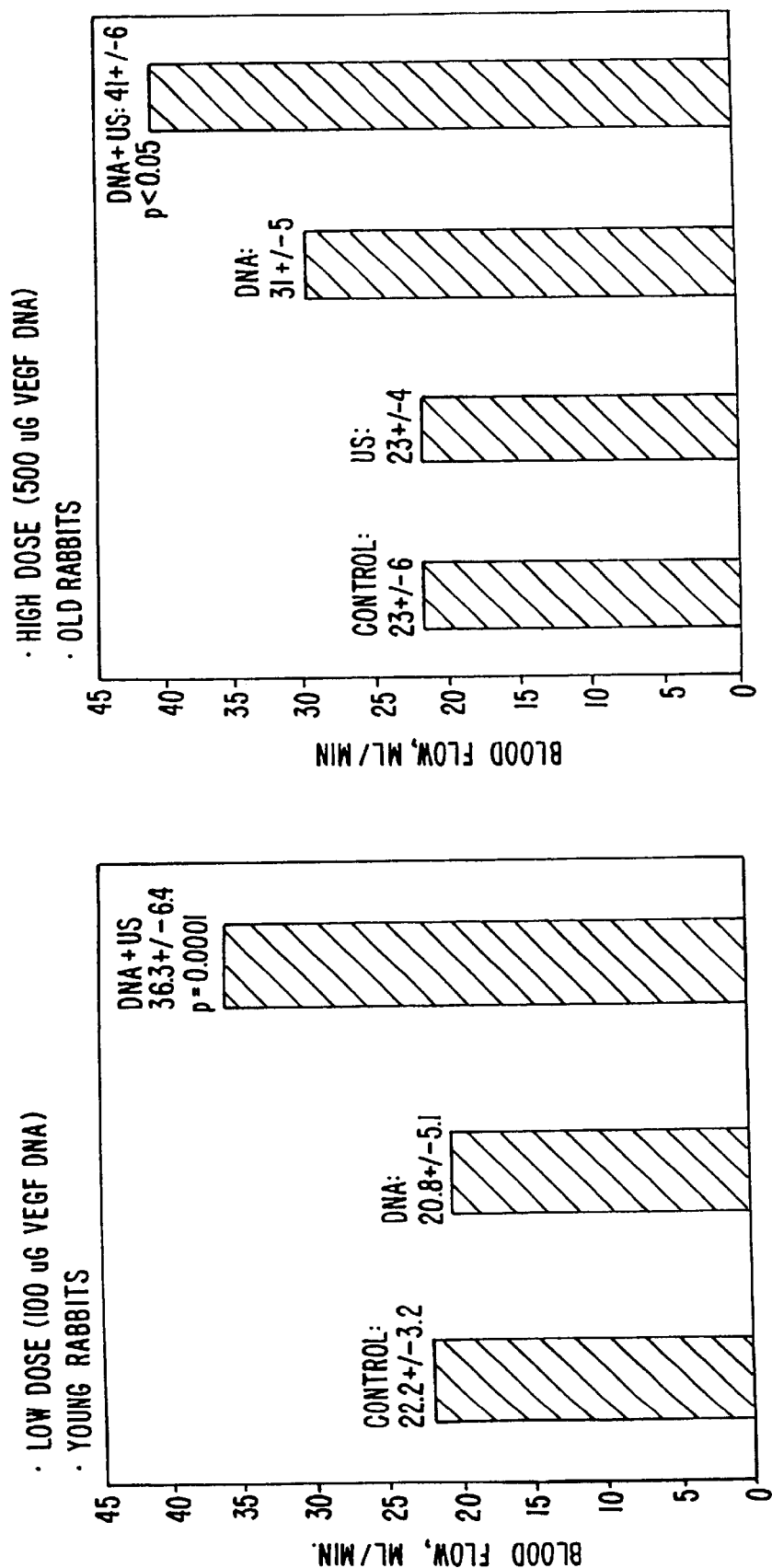
FIG. 31 graphically presents blood flow data for rabbit ischemic hind limb experiments.
Figure 32:
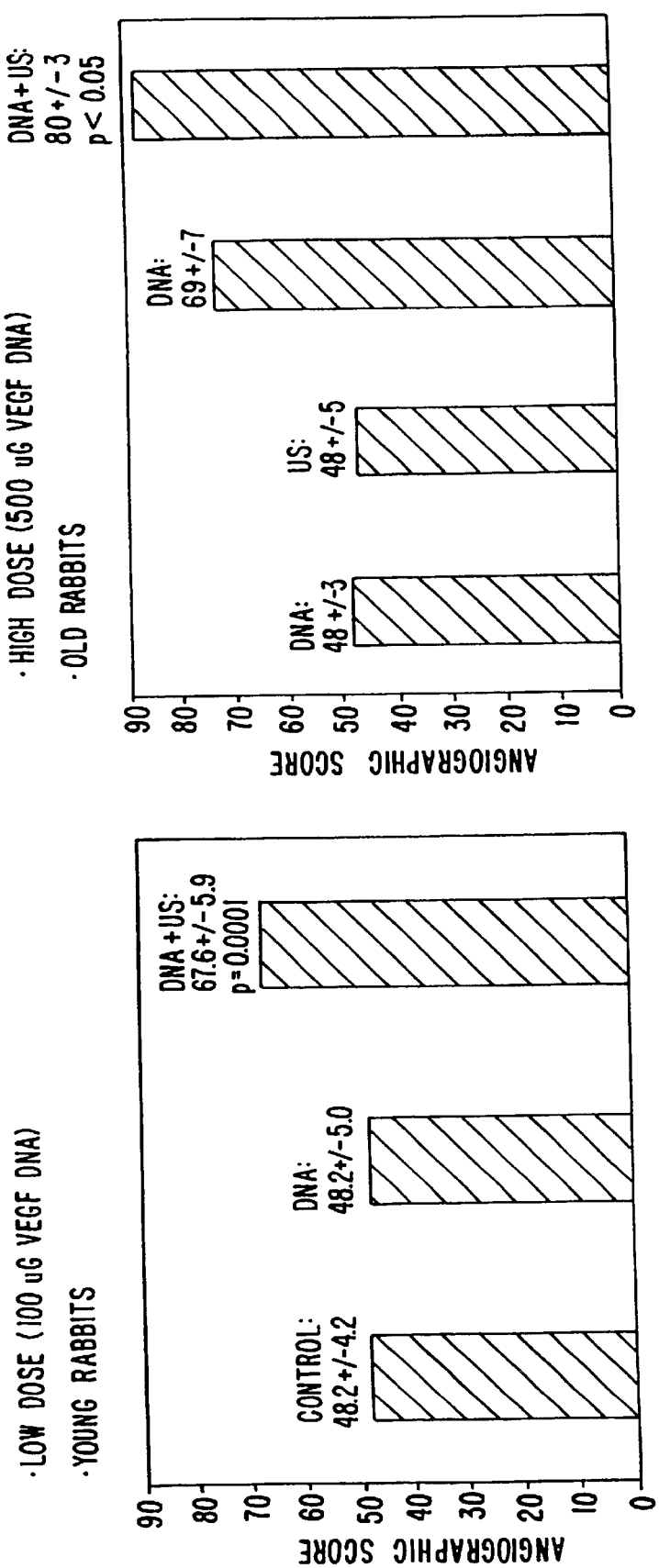
FIG. 32 graphically presents angiographic score data for rabbit ischemic hind limb experiments.

FIG. 29 depicts the experimental blood pressure ratio results, where the blood pressure ratio is derived from blood pressure measurements at the ankle of the ischemic hind limb and the contra-lateral normal hind limb. In both the young and old rabbits, the ischemic hind limb without ultrasound treatment remained at 50 percent of normal, the value most probably reflecting flow through the untouched external femoral artery. In the old rabbits, treatment with ultrasound alone did not result in a greater blood pressure than in the control ischemic hind limb. In young rabbits, VEGF expressing plasmid DNA treatment without ultrasound did not result in increased blood pressure, while in the old rabbits, the increased volume of injection showed a modest improvement in pressure. Lastly, in the case of both the young and old rabbits, the combination of VEGF expressing plasmid DNA and ultrasound resulted in substantial improvement in blood pressure, almost to normal values. These data suggest that there exists substantial benefit from the combination of DNA injections and ultrasound treatment. FIGS. 31 and 32 depict blood flow and angiographic score results, respectively, for the same experiments, clearly supporting the blood pressure results.

Experiment Number Three

As is described in copending U.S. patent application Ser. No. 09/223,230, a series of in vivo catheter experiments on the porcine animal model, in which it was found that the strength of the ultrasonic energy and the duration could be selected to provide a highly effective hyperplasia inhibition in the neointimal layer without significant damage to surrounding tissues or structures within an artery, were performed.

In particular, by exposing an arterial target site at risk of neointimal hyperplasia to a vibrational energy having a mechanical index in the range from 0.1 to 50, preferably from 0.2 to 10, and more preferably from 0.5 to 5, for a treatment time in the range from 10 seconds to 1000 seconds, preferably from 30 seconds to 500 seconds, and more preferably from 60 seconds to 300 seconds, the proliferation of vascular smooth muscle cells in the neointimal layer of the artery can be reduced by at least 2% (in comparison with untreated controls) after seven days, often at least 4%, and sometimes 6% or greater.

The resulting reduction in hyperplasia mass after 28 days will typically be at least 10%, usually at least 20%, and preferably at least 30%. Such inhibitions can be achieved without significant necrosis of the smooth muscle cells.

Broad, preferred, and exemplary values for each of these perimeters are set forth in table 3.

TABLE 3

PREFERRED AND EXEMPLARY TREATMENT CONDITIONS

| | BROAD | PREFERRED | EXEMPLARY |
|---|---|---|---|
| Mechanical Index (MI) | 0.1 to 50 | 0.2 to 10 | 0.5 to 5 |
| Intensity (SPT, W/cm$^2$) | 0.01 to 100 | 0.1 to 20 | 0.5 to 5 |
| Frequency (kHz) | 100 to 5000 | 300 to 3000 | 500 to 1500 |
| Elapsed Time (sec.) | 10 to 900 | 30 to 500 | 60 to 300 |
| Duty Cycle (%) | 0.1 to 100 | 0.2 to 10 | 0.2 to 2 |
| Pulse Repetition Frequency (PRF)(Hz) | 10 to 10,000 | 100 to 5000 | 300 to 3000 |

While the experiments in the subject application were conducted with catheter based ultrasound, similar results could be obtained with transcutaneous administration by operating the present invention to provide a suitable uniform field of ultrasound energy over a wide target region.

Experiment Number Four

As is described in copending U.S. patent application Ser. No. 09/345,661, transcutaneous ultrasonic energy in the form of the device of FIG. 11 (as also used for the VEGF and beta-galactosidase experiments) was applied in the surgical incision on sheep during the creation of a fistula between the femoral arteries and veins and the implantation of a graft between the carotid artery and the jugular vein. Each surgical site had three ultrasound exposures, the first directly on the center of the site, followed by proximal and distal exposures. Each ultrasound exposure featured a beam width of approximately 10 mm, for 120 seconds, at an MI level of approximately 3.0, with a duty cycle of one percent (30 cycles at 315 Hz repetition rate) and for a calculated increase in tissue temperature of less than 3 degrees Centigrade.

All control and ultrasound treated grafts and fistulas remained patent one month after creation. Measurements of intimal thickness (including intimal hyperplasia) on the venous side of the grafts showed progressively decreasing intimal thickness moving distally from the graft, with less growth in the ultrasound treated group. On the venous side of the fistulas, maximal intimal thickness plus organized thrombus was 0.45±0.22 mm in the control group and 0.18±0.21 mm in the treated group. This difference was statistically significant.

More specifically, by exposing the vascular target site at risk of neointimal hyperplasia to a uniform exposure of transcutaneous, (or percutaneous), ultrasound in the range of 1 MHz, 3.0 MI and 1% duty cycle, the hyperplasic effect on the vascular wall was blunted.

A common factors in these four experiments (three different animal models) was the need to sonicate a large region of tissue. A common result was the beneficial impact of therapeutic ultrasound.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of enhancing transfection of DNA delivered into a target region of a patient's body, comprising:
   delivering the DNA into the target region; and
   applying a uniform field of ultrasound energy across a wide area of the target region, the ultrasound energy being of a type and an amount sufficient to enhance transfection of the DNA in the target region, wherein the uniform field comprises
   a field which varies in intensity by at least one of (1) less than 10 dB in a lateral direction across the width of the field, and (2) less than 10 dB in an axial direction across the depth of the target region.

2. The method of claim 1, wherein the DNA comprises an expression vector.

3. The method of claim 1, wherein the DNA expresses a protein from the group consisting of VEGF, EPO, Factor VIII, Factor IX, angiostatin and endostatin (as filed) the method of claim 1, wherein the ultrasound energy is sufficiently strong to cause DNA transfection, yet is sufficiently weak to prevent DNA fractionation.

4. The method of claim 1, wherein the ultrasound energy is sufficiently strong to cause DNA transfection, yet is sufficiently weak to prevent DNA fractionation.

5. The method of claim 1, wherein, the DNA is injected intramuscularly as a bolus into the target region.

6. The method of claim 1, wherein the uniform field comprises at least a field which varies in intensity by less than 10 dB in a lateral direction across the width of the field.

7. The method of claim 1, wherein the uniform field comprises at least a field which varies in intensity by less than 6 dB in a lateral direction across the width of the field.

8. The method of claim 1, wherein the uniform field comprises at least a field which varies in intensity by less than 3 dB in a lateral direction across the width of the field.

9. The method of claim 1, wherein the uniform field comprises at least a field which varies in intensity by less than 10 dB in an axial direction across the depth of the target region.

10. The method of claim 1, wherein the uniform field comprises at least a field which varies in intensity by less than 6 dB in an axial direction across the depth of the target region.

11. The method of claim 1, wherein the uniform field comprises at least a field which varies in intensity by less than 3 dB in an axial direction across the depth of the target region.

12. The method of claim 11, wherein the ultrasound energy has a mechanical index of 0.1 to 20.

13. The method of claim 1, wherein the ultrasound energy has a mechanical index of 0.3 to 15.

14. The method of claim 1, wherein the ultrasound energy has a mechanical index of 0.5 to 10.

15. The method of claim 1, wherein the ultrasound energy has a mechanical index of 0.5 to 5.

16. The method of claim 1, wherein the ultrasound energy has a transient thermal index less than 4.

17. The method of claim 1, wherein the ultrasound energy is applied with a duty cycle of 0.1 to 50%.

18. The method of claim 1, wherein the ultrasound energy is applied with a duty cycle of 0.3 to 20%.

19. The method of claim 1, wherein the ultrasound energy is applied with a duty cycle of 0.5 to 5%.

20. The method of claim 1, wherein the ultrasound energy is applied at a frequency of 20 kHz to 5 MHz.

21. The method of claim 1, wherein the ultrasound energy is applied at frequency of 100 kHz to 1.5 MHz.

22. The method of claim 1, wherein the ultrasound energy field has a beam width of at least 0.5 cm.

23. The method of claim 1, wherein the ultrasound energy field has a beam width of at least 1.2 cm.

24. The method of claim 1, wherein the ultrasound energy field has a beam width of at least 3.5 cm.

25. The method of claim 1, wherein the target region has a transdermal depth of 1 to 4 cm.

26. The method of claim 1, wherein applying a uniform field of ultrasound energy comprises:

contacting a window of a housing on a patient's skin; and driving an ultrasound transducer mounted within the housing to deliver the ultrasound energy.

27. The method of claim 1, wherein the uniform field of ultrasound is applied across the wide area of the target region concurrently with delivering the DNA into the target region.

28. The method of claim 1, wherein the uniform field of ultrasound is applied across the wide area of the target region before delivering the DNA into the target region.

29. The method of claim 1, wherein the uniform field of ultrasound is applied across the wide area of the target region immediately after delivering the DNA into the target region.

30. The method of claim 1, wherein the uniform field of ultrasound is applied across the wide area of the target region 15 to 60 minutes time after delivering the DNA into the target region.

31. A kit for enhancing transfection of DNA delivered into a target region of a patient's body, comprising:

an ultrasound energy delivery system; and instructions for use setting forth the method of claim 1.

* * * * *